US009310291B2

(12) United States Patent
Schulz et al.

(10) Patent No.: US 9,310,291 B2
(45) Date of Patent: Apr. 12, 2016

(54) REACTION VESSEL FOR CARRYING OUT ARRAY PROCESSES

(75) Inventors: Torsten Schulz, Jena (DE); Eugen Ermantraut, Jena (DE); Ralf Ehricht, Jena (DE); Klaus-Peter Möbius, Zöllnitz (DE); Gerd Wagner, Jena (DE); Joachim Fischer, Portstendorf (DE); Thomas Ellinger, Jena (DE)

(73) Assignee: CLONDIAG CHIP TECHNOLOGIES GMBH, Jena (DE)

( * ) Notice: Subject to any disclaimer, the term of this patent is extended or adjusted under 35 U.S.C. 154(b) by 0 days.

(21) Appl. No.: 10/892,743

(22) Filed: Jul. 16, 2004

(65) Prior Publication Data
US 2005/0064469 A1    Mar. 24, 2005

Related U.S. Application Data

(63) Continuation of application No. PCT/EP03/00408, filed on Jan. 16, 2003.

(30) Foreign Application Priority Data

Jan. 16, 2002  (DE) .................................. 102 01 463

(51) Int. Cl.
*G01N 21/25* (2006.01)
*B01L 3/00* (2006.01)
(Continued)

(52) U.S. Cl.
CPC ................ *G01N 21/253* (2013.01); *B01L 3/50* (2013.01); *B01L 3/5082* (2013.01); *B01L 7/52* (2013.01); *C12Q 1/6837* (2013.01); *G01N 33/54366* (2013.01); *B01J 2219/0054* (2013.01);
(Continued)

(58) Field of Classification Search
CPC ....... G01N 21/253; B01L 3/50; B01L 3/5082; B01L 7/52
USPC ................ 422/50, 55, 61, 68.1, 82.05, 82.07; 435/4, 7.1, 283.1, 287.1, 287.2, 288.3, 435/288.4, 288.7; 436/164, 172
See application file for complete search history.

(56) References Cited

U.S. PATENT DOCUMENTS 4,224,304 A * 9/1980 Sawai et al. .................... 436/517
4,498,780 A * 2/1985 Banno et al. ................... 356/414
(Continued)

FOREIGN PATENT DOCUMENTS

DE         37 17 209 A     12/1988
EP         0 235 726       9/1987
(Continued)

OTHER PUBLICATIONS

Websters Merriam, Websters Ninth New Collegiate Dictionary, 1983, Merriam-Webster Inc, Ninth Ed, p. 1269.*
(Continued)

Primary Examiner — Melanie Y Brown
(74) Attorney, Agent, or Firm — Steptoe & Johnson LLP

(57) ABSTRACT

The invention relates to a reaction vessel, a device and a method for detecting specific interactions between molecular target and probe molecules. The present invention especially relates to a reaction vessel which has a shape and size typical of a laboratory reaction vessel and in which a supporting element with probe molecules immobilized thereon on predetermined regions is arranged on its base surfaces.

54 Claims, 12 Drawing Sheets

(51) Int. Cl.
  B01L 7/00     (2006.01)
  C12Q 1/68     (2006.01)
  G01N 33/543   (2006.01)
  C40B 40/06    (2006.01)
  C40B 60/14    (2006.01)
  C40B 70/00    (2006.01)

(52) U.S. Cl.
  CPC ............... *B01J2219/00283* (2013.01); *B01J 2219/00529* (2013.01); *B01J 2219/00585* (2013.01); *B01J 2219/00596* (2013.01); *B01J 2219/00707* (2013.01); *B01J 2219/00722* (2013.01); *B01L 2300/0636* (2013.01); *B01L 2300/0851* (2013.01); *C40B 40/06* (2013.01); *C40B 60/14* (2013.01); *C40B 70/00* (2013.01)

(56) References Cited

U.S. PATENT DOCUMENTS

| | | | |
|---|---|---|---|
| 4,994,373 A | | 2/1991 | Stavrianopoulos et al. |
| 5,012,941 A | * | 5/1991 | Abrams et al. ............... 215/250 |
| 5,362,624 A | | 11/1994 | Schmitt et al. |
| 5,464,112 A | * | 11/1995 | Guillot ......................... 215/254 |
| 5,683,875 A | | 11/1997 | Lichtenwalter |
| 5,784,152 A | | 7/1998 | Heffelfinger et al. |
| 5,914,245 A | | 6/1999 | Bylina et al. |
| 6,040,171 A | * | 3/2000 | Ho et al. ..................... 435/288.1 |
| 6,083,763 A | * | 7/2000 | Balch ............................ 436/518 |
| 6,218,132 B1 | * | 4/2001 | Spack et al. ................. 435/7.24 |
| 6,309,608 B1 | * | 10/2001 | Zhou et al. ...................... 506/40 |
| 6,756,224 B2 | * | 6/2004 | Vischer ........................... 506/9 |
| 6,770,441 B2 | * | 8/2004 | Dickinson et al. ................ 435/6 |
| 6,930,314 B2 | * | 8/2005 | Jackson et al. .............. 250/458.1 |
| 6,933,109 B2 | * | 8/2005 | Anderson ......................... 435/5 |
| 7,001,572 B1 | * | 2/2006 | Gueritault et al. ............ 422/68.1 |
| 7,008,788 B2 | * | 3/2006 | Schremp et al. ........... 435/287.1 |
| 7,211,433 B1 | * | 5/2007 | Dahm et al .................... 435/325 |
| 2003/0026739 A1 | * | 2/2003 | MacBeath et al. ............ 422/102 |
| 2003/0049862 A1 | * | 3/2003 | He et al. ........................ 436/180 |
| 2003/0098271 A1 | * | 5/2003 | Somack et al. ............... 210/295 |

FOREIGN PATENT DOCUMENTS

| | | |
|---|---|---|
| EP | 0344 578 A | 12/1989 |
| WO | WO99/60381 | 11/1999 |

OTHER PUBLICATIONS

International Search Report, Mar. 11, 2003.
Marshall A., et al.; DNA Chips: An Array of Possibilities, Nature Biotechnology, vol. 16, pp. 27-31, (1998).
Ramsay, G.; DNA Chips: State of the Art, Nature Biotechnology, vol. 16, pp. 40-44, (1998).
Lockhart, D.J. et al.; Genomics, Gene Expression and DNA Arrays, Nature, vol. 405, pp. 827-836, (2000).

* cited by examiner

| M | M | M | M | | | M |
|---|---|---|---|---|---|---|
| G2064A-WT+2 | G2064A+2 | | G2064A-WT+4 | G2064A+4 | | |
| G2064A-WT-2 | G2064A-2 | | G2064A-WT-4 | G2064A-4 | | |
| G1934A-WT+4 | G1934A+4 | | G2064A-WT | G2064A | | |
| G1934A-WT-4 | G1934A-4 | | G1934A-WT+2 | G1934A+2 | | |
| G1934A-WT | G1934A | | G1934A-WT-2 | G1934A-2 | | |
| dT1795-WT+2 | dT1795+2 | | dT1795-WT+4 | dT1795+4 | | |
| dT1795-WT-2 | dT1795-2 | | dT1795-WT-4 | dT1795-4 | | |
| G1749C-WT+4 | G1749C+4 | | dT1795-WT | dT1795 | | |
| G1749C-WT-4 | G1749C-4 | | G1749C-WT+2 | G1749C+2 | | |
| G1749C-WT | G1749C | | G1749C-WT-2 | G1749C-2 | | |
| M | | | | | | M |

SEQUENCE LISTING

```
<160> NUMBER OF SEQ ID NOS: 42

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcttctccgt gtccaccttg c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcttctccgt ctccaccttg c                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 3
gcgcttctcc gtgtccacct t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcgcttctcc gtctccacct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aggcgcttct ccgtgtccac c                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aggcgcttct ccgtctccac c                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttctccgtgt ccaccttgcg c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttctccgtct ccaccttgcg c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 9
ctccgtgtcc accttgcgca a                                          21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctccgtctcc accttgcgca a                                          21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gctggagcag tgggtgaccg a                                          21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gctggagcag gggtgaccga g                                          21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcgctggagc agtgggtgac c                                          21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcgctggagc agggggtgacc g                                         21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 15
agtcgctgga gcagtgggtg a                                            21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agtcgctgga gcagggtga c                                             21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tggagcagtg ggtgaccgag g                                            21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tggagcaggg gtgaccgagg a                                            21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gagcagtggg tgaccgagga g                                            21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gagcaggggt gaccgaggag g                                            21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 21
cccaccccca ggacgccct t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cccaccccca agacgccct t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ctcccacccc caggacgccc c                                             21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctcccacccc caagacgccc c                                             21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atctcccacc cccaggacgc c                                             21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atctcccacc cccaagacgc c                                             21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 27 caccccagg acgccctttt c                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cacccccaag acgccccttt c                                             21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cccccaggac gcccctttcg c                                             21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cccccaagac gcccctttcg c                                             21

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tagctcagga gggactgaag gagga                                         25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tagctcagga ggaactgaag gagga                                         25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 33
cctagctcag gagggactga aggag                                    25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cctagctcag gaggaactga aggag                                    25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gacctagctc aggagggact gaagg                                    25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gacctagctc aggaggaact gaagg                                    25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gctcaggagg gactgaagga ggagt                                    25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gctcaggagg aactgaagga ggagt                                    25

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 39
tcaggaggga ctgaaggagg agtcg                                           25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcaggaggga ctgaaggagg agtcg                                           25

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cacgcgcacg tgcccgtccc a                                               21

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctctcgctcc gcacctcgcg caga                                            24
```

REACTION VESSEL FOR CARRYING OUT ARRAY PROCESSES

BACKGROUND OF THE INVENTION

Biomedical tests are frequently based on detecting an interaction between a molecule, which is present in known quantity and position (i.e. the molecular probe) and an unknown molecule to be detected or unknown molecules to be detected (i.e. the molecular target molecules). In modern tests the probes are deposited in the form of a substance library on supports, the so-called micro-arrays or chips so that one sample can be analysed simultaneously in parallel on a plurality of probes (D. J. Lockhart, E. A. Winzeler, Genomics, gene expression and DNA arrays; Nature 2000, 405, 827-836). In order to fabricate the micro-arrays the probes are usually immobilised in a predetermined manner on a suitable matrix, described for example in WO 00/12575 (see for example U.S. Pat. No. 5,412,087, WO 98/36827) or are produced synthetically (see for example U.S. Pat. No. 5,143,854).

The interaction between the probe and the target molecule is usually detected as follows: after fixing the probe or the probes in a predetermined manner on a specific matrix in the form of a micro-array, the targets are brought in contact with the probes in a solution and incubated under defined conditions. As a result of the incubation, a specific interaction takes place between probe and target. The binding observed in this case is definitely more stable than the binding of target molecules to probes which are not specific for the target molecule. In order to remove target molecules which have not been specifically bound, the system is washed with suitable solutions or heated.

The specific interaction between a target and its probe can then be detected by a plurality of methods which generally depend on the type of marker which has been incorporated into target molecules before, during or after the interaction of the target molecule with the micro-array. Such markers typically comprise fluorescent groups so that specific target/probe interactions can be read out using fluorescence optics with high spatial resolution and at little expenditure compared with other conventional detection methods, particularly mass-sensitive methods (A. Marshall, J. Hodgson, DNA chips: An array of possibilities, Nature Biotechnology 1998, 16, 27-31; G. Ramsay, DNA Chips: State of the art, Nature Biotechnology 1998, 16, 40-44).

Depending on the substance library immobilised on the micro-array and the chemical nature of the target molecules, interactions between nucleic acids and nucleic acids, between proteins and proteins as well as between nucleic acids and proteins can be investigated using this test principle (for a review see F. Lottspeich, H. Zorbas, 1998, Bioanalytik, Spektrum Akademischer Verlag, Heidelberg Berlin).

Antibody libraries, receptor libraries, peptide libraries and nucleic acid libraries can be considered as substance libraries that can be immobilised on micro-arrays or chips.

The nucleic acid libraries play by far the most important role. These are micro-arrays on which deoxyribonucleic acid (DNA) molecules or ribonucleic acid (RNA) molecules are immobilised.

A prerequisite for the binding of a target molecule in the form of a DNA or RNA molecule and labelled with a fluorescence group to a nucleic acid probe of the micro-array is that both the target molecule and also the probe molecule are present in the form of a single-stranded nucleic acid. Efficient and specific hybridisation can only take place between such molecules. Single-stranded nucleic acid target molecules and nucleic acid probe molecules are generally obtained by heat denaturing and optimal choice of parameters such as temperature, ionic strength and concentration of helix-destabilising molecules. It is thus ensured that only probes with almost perfectly complementary sequences, i.e., corresponding to one another, remain paired with the target sequence (A. A. Leitch, T. Schwarzacher, D. Jackson, I. J. Leitch, 1994, In vitro Hybridisierung, Spektrum Akademischer Verlag, Heidelberg Berlin Oxford).

A typical example for the use of micro-arrays in biological test methods is the detection of micro-organisms in samples in biomedical diagnostics. In this case, use is made of the fact that the genes for ribosomal RNA (rRNA) are ubiquitously distributed and have sequence sections which are characteristic for the particular species. These species-specific sequences are deposited on a micro-array in the form of single-stranded DNA oligonucleotides. The target DNA molecules to be analysed are first of all isolated from the sample to be analysed and are provided with markers, for example fluorescent labels. The thus labelled target DNA molecules are then incubated in a solution with the probes deposited on the micro-array, non-specifically occurring interactions are removed by suitable washing steps and specific interactions are detected by fluorescence optical evaluation. In this way it is possible to detect for example a plurality of micro-organisms simultaneously in one sample. In this test method the number of detectable micro-organisms theoretically only depends on the number of specific probes which have been deposited on the micro-array.

For the practical implementation of these tests the micro-arrays or chips are fixed in closed chambers having inlets and outlets for changing liquids required for the washing and hybridisation steps. Such systems are described for example in U.S. Pat. No. 6,287,850 and WO 01/02094. DE 199 40 750 describes a support for analyte determining methods which following slight design modifications is suitable for use in array applications within the context of this invention.

Surface-bound DNA libraries which are deposited on slides are usually used for DNA sequence analysis. So far, special hybridisation chambers or incubation chambers have been used for carrying out the hybridisation reaction on these slides. In order to ensuring the tempering and mixing of the hybridisation solution in these hitherto known chambers, equipment specially adapted for the device used, which is therefore expensive and costly, is required.

DE 101 49 684.2 describes a flow cell which is suitable for carrying out a PCR as well as hybridisation reactions on DNA chips. The flow cell described therein is a complex structural element which is provided with a number of technical features which preclude the use of equipment conventionally used in laboratories such as a thermomixer for example (Eppendorf, Germany, Hamburg) or a laboratory centrifuge (Heraeus, Hanau, Germany).

WO 01/02094 describes a cartridge which comprises a DNA chip. In this cartridge both a PCR and a hybridisation reaction can be carried out on a DNA chip. WO 95/33846 describes a body with a recess in which a substrate with nucleic acid molecules of known sequence is deposited on predetermined regions. The body has a sealed cavity into which sample liquid can be injected. The filling channels are sealed up using septa and are opened with injection cannulae to fill the body or the cartridge. The use of the cartridges described hereinbefore likewise requires apparatus specifically provided for this purpose.

U.S. Pat. No. 5,856,174 describes a miniaturised integrated nucleic acid diagnostics device. This device can be used for the collection of one or a plurality of samples, their preparation and the subsequent execution of a plurality of sample analyses. Such a device can be used for automatically carrying out a DNA-chip-based analysis by combining and miniaturising all the steps incurred on a cartridge. The provision of such a device is extremely expensive and costly.

U.S. Pat. No. 5,545,531 describes a method for manufacturing microtitre plates whose bottom is a wafer which has a sample matrix at each position at which a recess is located in the microtitre plate. U.S. Pat. No. 5,874,219 describes a method for the concurrent performance of biological tests in which a plurality of reaction vessels are arranged coherently next to one another and each vessel is provided with a molecular sample matrix. This biological chip reaction vessel plate is configured such that the interactions on the molecular sample matrix can be read out with suitable readers. In this way, a number of biological samples can be investigated next to one another and parallel with molecular sample matrices. The reaction vessel plate described there is not suitable for carrying out individual tests. The manufacture of such a reaction vessel plate is described in U.S. Pat. No. 5,545,531.

In the light of the prior art described hereinbefore it is obvious that there is a great need for apparatus which on the one hand can be provided simply and cost-effective and on the other hand, can be used for carrying out micro-array-based detection tests simply. In particular, there is a need for devices for carrying out micro-array-based tests which allows the use of typical equipment and instruments in everyday use in the laboratory. In general, there is a need for equipment for carrying out micro-array-based tests which is distinguished by a simple design, easy handling, avoidance of contamination sources, carrying out reproducible tests and low manufacturing costs.

At the present time, analyses based on probe arrays are thus generally read out using fluorescence optics (see A. Marshall and J. Hodgson, DNA Chips: An array of possibilities, *Nature Biotechnology*, 16, 1998, 27-31; G. Ramsay, DNA Chips: State of the Art, *Nature Biotechnology*, 16, January 1998, 40-44). A disadvantage with the conventional detection methods, however, is the considerable technical effort in some cases and the high costs associated with the detection method.

Recently a number of array methods have been developed which allow qualitative and/or quantitative detection of the interaction between probes and targets with relatively low technical effort.

DE 100 33 334.6 and WO 02/02810 describe methods for the quantitative and qualitative detection of molecular interactions on probe arrays by time-resolved precipitation reactions as well as the relevant equipment and single-use articles.

WO 99/35499 describes a device in which substance libraries are addressably deposited on a disk which is similar to a modern compact disk (CD). A certain substance on the disk can be approached by rotating the disk. The read head of the reader can then be moved along the radius of the disk. The position of the disk can be determined by tracks which are integrated and which can be read out with a standard CD player. The interaction of the sample with a target substance can be accomplished by absorption measurements and fluorescence measurements in transmitted or incident light. Equally, magnetic particles which can be detected using a magnetic read head can be deposited. In order to visualise the interaction reaction, staining by a silver precipitate is especially proposed, whose precipitation is mediated by a streptavidin/biotin-gold conjugate.

WO 00/72018 discloses a method for the precipitation of silver on slides for visualising interaction reactions of substance libraries. The readers required for this purpose are also described.

SUMMARY OF THE INVENTION

It is thus the object of the present invention to provide a device for carrying out array methods which is distinguished by its simple construction, easy handling and thus cost-effective manufacture. Another object of the present invention is to provide a reaction vessel which can be used in such a device and which is also distinguished by easy handling and by compatibility with equipment usually used in laboratories such as table-top centrifuges and pipettes. It is furthermore an object of the invention to provide a reaction vessel which allows micro-array-based tests to be carried out in a single-chamber system avoiding sources of contamination. Moreover, it is an object of the present invention to provide a device for carrying out array methods which allows the use of detection methods with relatively low technical effort.

These and further objects of the present invention are solved by providing the subject matter specified in the claims. Preferred embodiments are defined in the dependent claims.

The objects are solved according to the invention by providing a reaction vessel which has a typical shape and/or typical size for a laboratory reaction vessel and wherein a supporting element with probe molecules immobilised on predetermined regions thereon is arranged on one of its base surfaces.

The use of the reaction vessel according to the invention for detecting specific interactions between molecular target and probe molecules has the important advantage that it is not necessary to purchase additional equipment or additional accessories to carry out the detection reactions since the equipment for standard laboratory reaction vessels usually used in laboratories, especially in biological laboratories, such as table-top centrifuges and pipettes for example, can be used. Another advantage of the reaction vessel according to the invention is that a separate incubation chamber is superfluous, since the reaction vessel also serves as a hybridisation chamber. In addition, the surface of the support with the probe molecules immobilised thereon is protected from contamination and other disadvantageous external influences by the lid locking or cap locking which is typical of conventional laboratory reaction vessels, for example the safe-lock cap locking of Eppendorf reaction vessels.

Light from an incoherent light source (1001) homogeneously illuminates the surface-bound DNA library on a library chip (100) located in a tube using illuminating optics (1002). The signal from a CCD camera (1005) is recorded using readout optics (1004).

Figure 5:
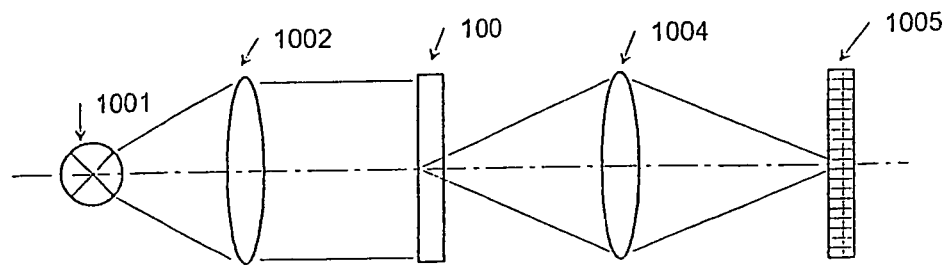
FIG. 5: Shows a fundamental arrangement for reading out an array in the reaction vessel according to the invention.
Figure 6:
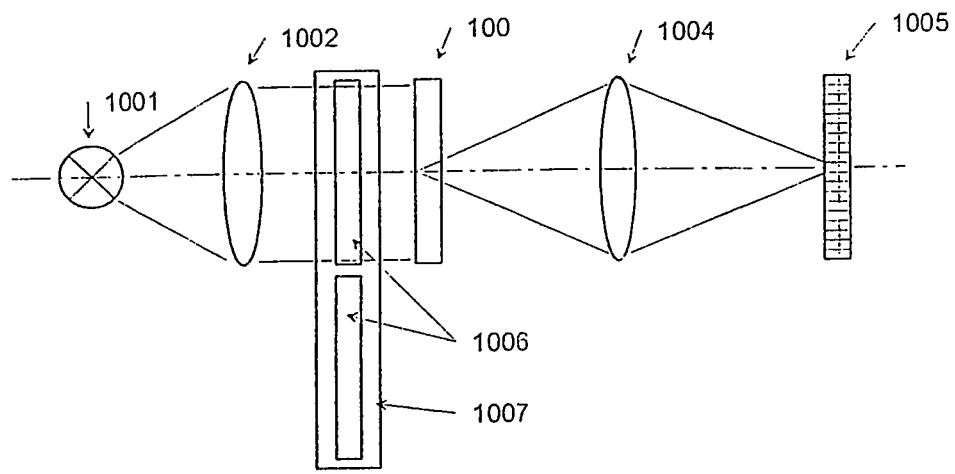

FIG. 6: Shows the same arrangement as in FIG. 5 with the variant of limiting the spectral range of the illumination by incorporating optical filters (1006) into the optical path of the illuminating beam. The opportunity of changing these filters quickly by means of filter changers (1007) has the advantage for the evaluation that any incorrect information which may occur e.g. as a result of contamination can be clearly identified and eliminated.

Figure 7:
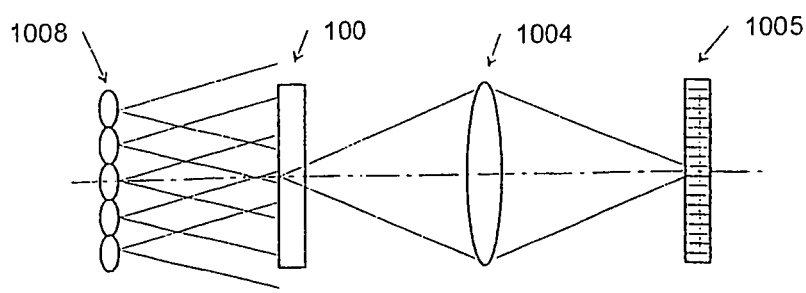

FIG. 7: In this embodiment the classical illumination is replaced by an illuminating array (1008). Preferably diffusely scattering LED arranged in a matrix form make it possible to achieve homogeneous illumination at short distances from the sample.

Figure 8:
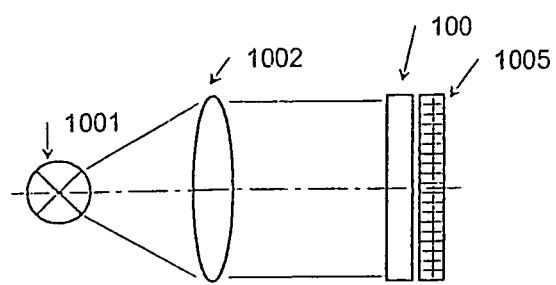

FIG. 8: Shows a compact form of the arrangement from FIG. 1 in which the CCD sensor (1005) of the camera is in direct contact with the affinity matrix (100). This contact can be made by using a fibreboard (1012) or at even greater distances by an image cable if direct contact is not possible.

Figure 9:
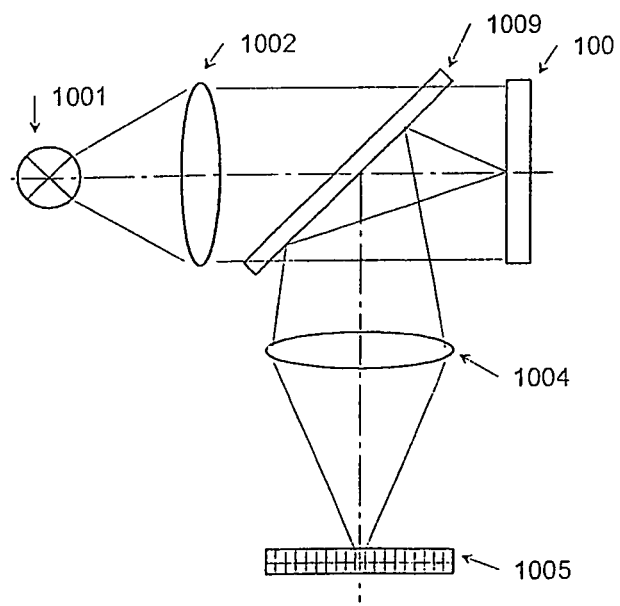

FIG. 9: Shows an arrangement for reading out the samples in incident light. In this case a semitransparent mirror (1009) is used.

Figure 10:
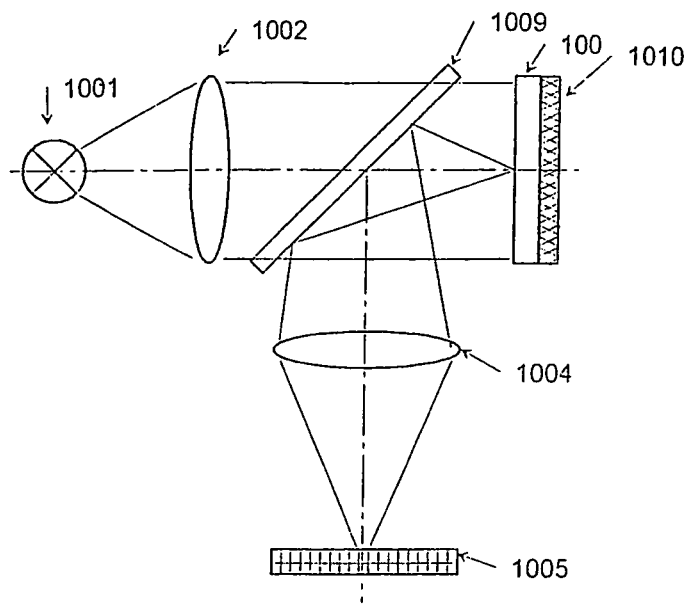

FIG. 10: Since the silver samples do not possess very good reflection properties, an arrangement as shown in this diagram is advantageous. Here the disadvantage of the poor reflection is supplemented by transmission effects wherein the illuminating light is reflected via a mirror layer (1010) either as an independent mirror or as a layer deposited on the backside of the sample support.

Figure 11:
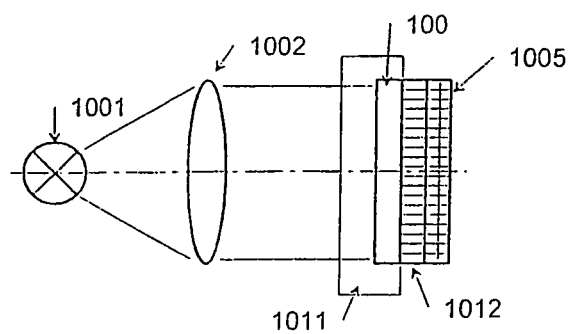

FIG. 11: Shows an arrangement in a transparent sample space, preferably in a cell (1011) which makes it possible to achieve good coupling of the receiver to the sample space by means of a fibreboard (1012) through the optically plane outer surfaces. Very compact sensors, such as those shown in FIG. 8, can be realised by using diffuse surface emitters (1013) based on electroluminescence or cold cathode fluorescence methods for example.

Figure 12:
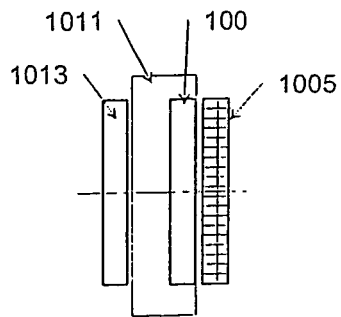

FIG. 12: Shows a very compact arrangement of the reader (1000) shown in FIG. 11.

Figure 13:
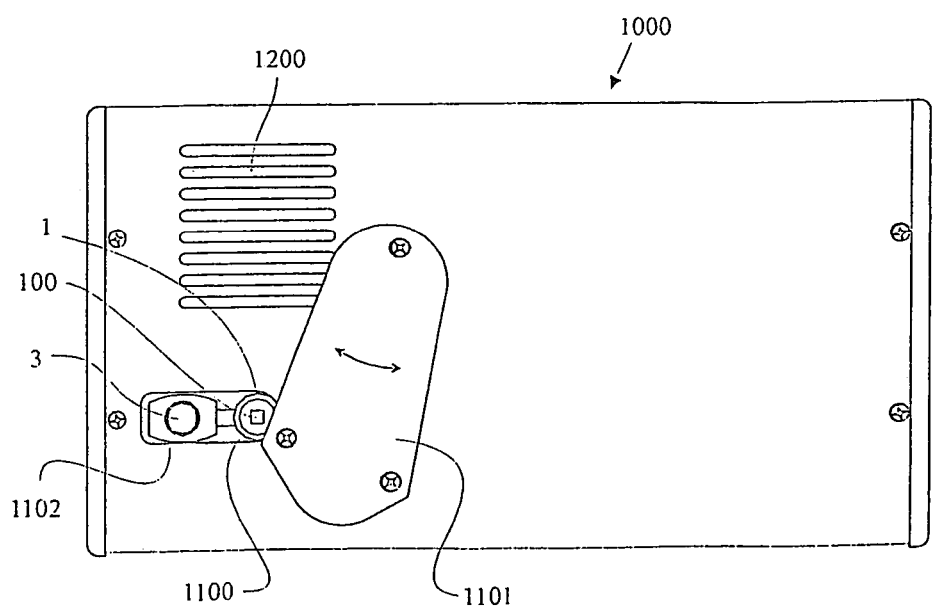

FIG. 13: Sectional view of a reader operating in accordance with the principle shown in FIG. 7 with the difference that a deflecting mirror was incorporated between the affinity matrix (100) and the imaging optics (1004) in order to obtain compact equipment dimensions. The light source (1008) consists of light-emitting diodes which are built into a swivel arm (1101) which can be swivelled aside for insertion of the reaction vessel (1) into the reader. It is then swivelled over the reaction vessel (1) in order to illuminate the affinity matrix (100).

Figure 14:
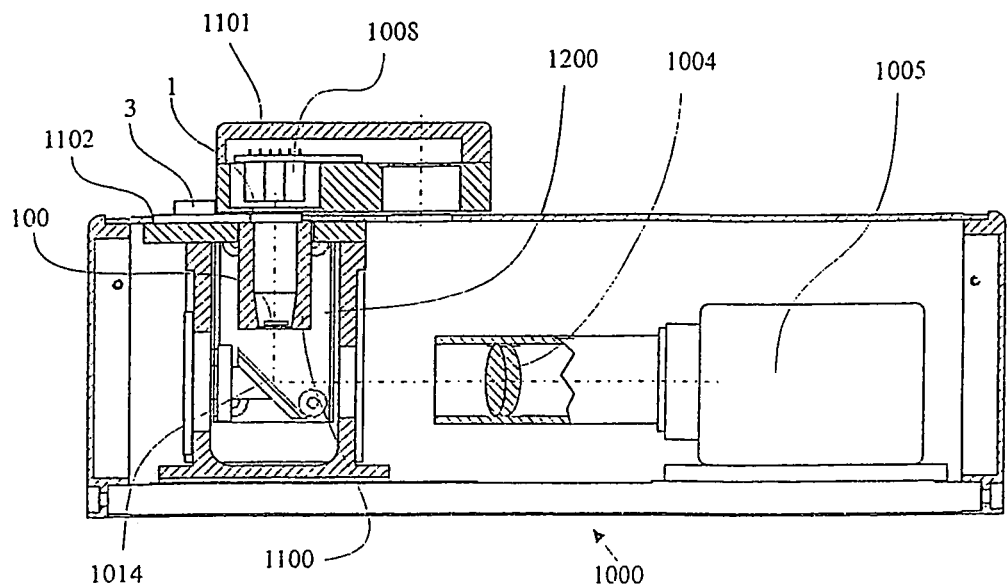

FIG. 14: Corresponds to FIG. 13 except that it is a plan view (from the operator side). Located on the top is an adjusting recess (1102) into which the lid of the reaction vessel (1) can be pressed. Twisting of the affinity matrix is thereby avoided.

Figure 15:
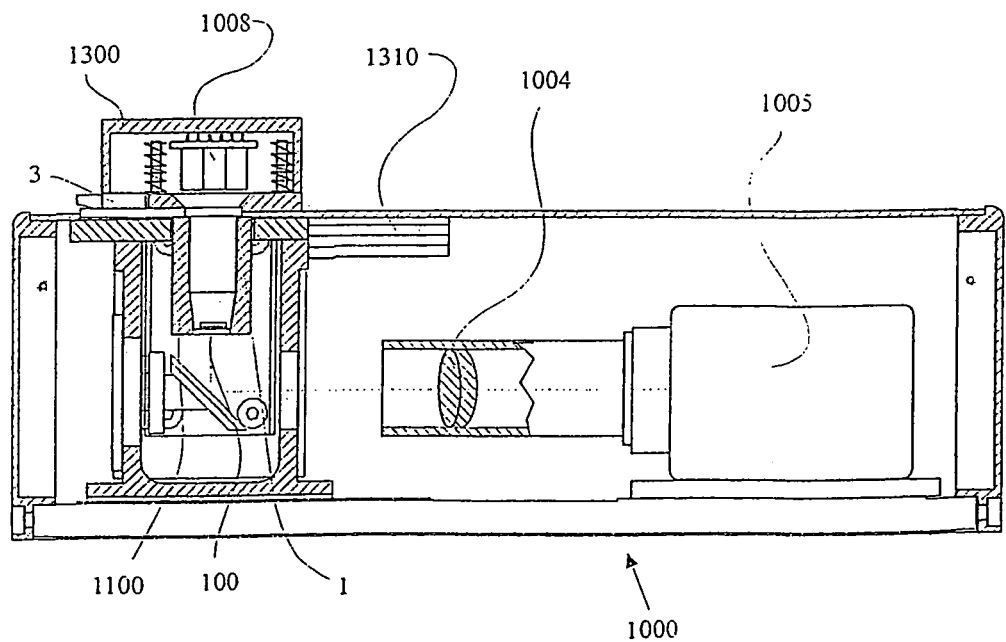

FIG. 15: A reader (1000) is shown which differs from that in FIG. 13 in that the swivel arm (1101) is replaced by a slider (1300). The slider (1300) is slid over the reaction vessel (1) via a linear bearing (1310). In this case, a moving carriage (1320) presses the reaction vessel (1) into the reaction vessel holder (1100).

Figure 16:
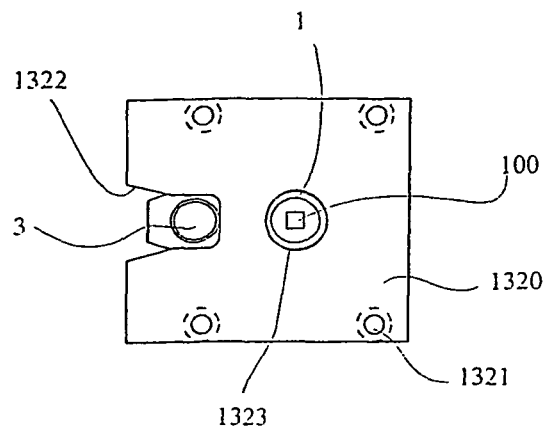

FIG. 16: The moving carriage (1320) of the slider (1300) is shown in plan view. The carriage (1320) is pushed by four compression springs (1321) onto the reaction vessel (1). An adjusting gap (1322) embraces the lid (3) of the reaction vessel (1) such that the reaction vessel (1) is turned into its correct position and is fixed.

Figure 17:
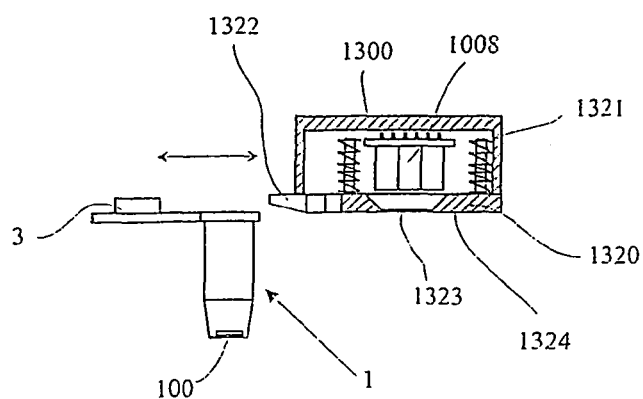

FIG. 17: The position of the slider (1300) with respect to the reaction vessel (1) with the reader opened is shown in cross-sectional view. The carriage (1300) moves along the arrow and thereby closes the reader. The slider consists of the compression springs (1321) which press down the carriage (1320) which has a detection opening (1323) through which the light from the light source (1001) can radiate.

Figures 18, 19:
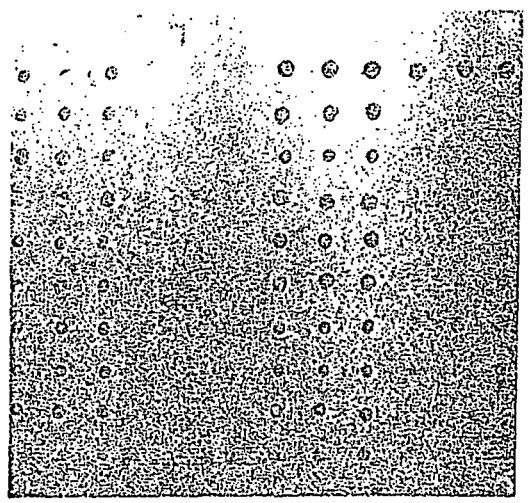

FIG. 18: Layout of the array (102) having the dimensions 2.4 mm×2.4 mm; the names of the threefold redundant probes are given in each case. "M"=marker/labelling/tag.

Figure 1:
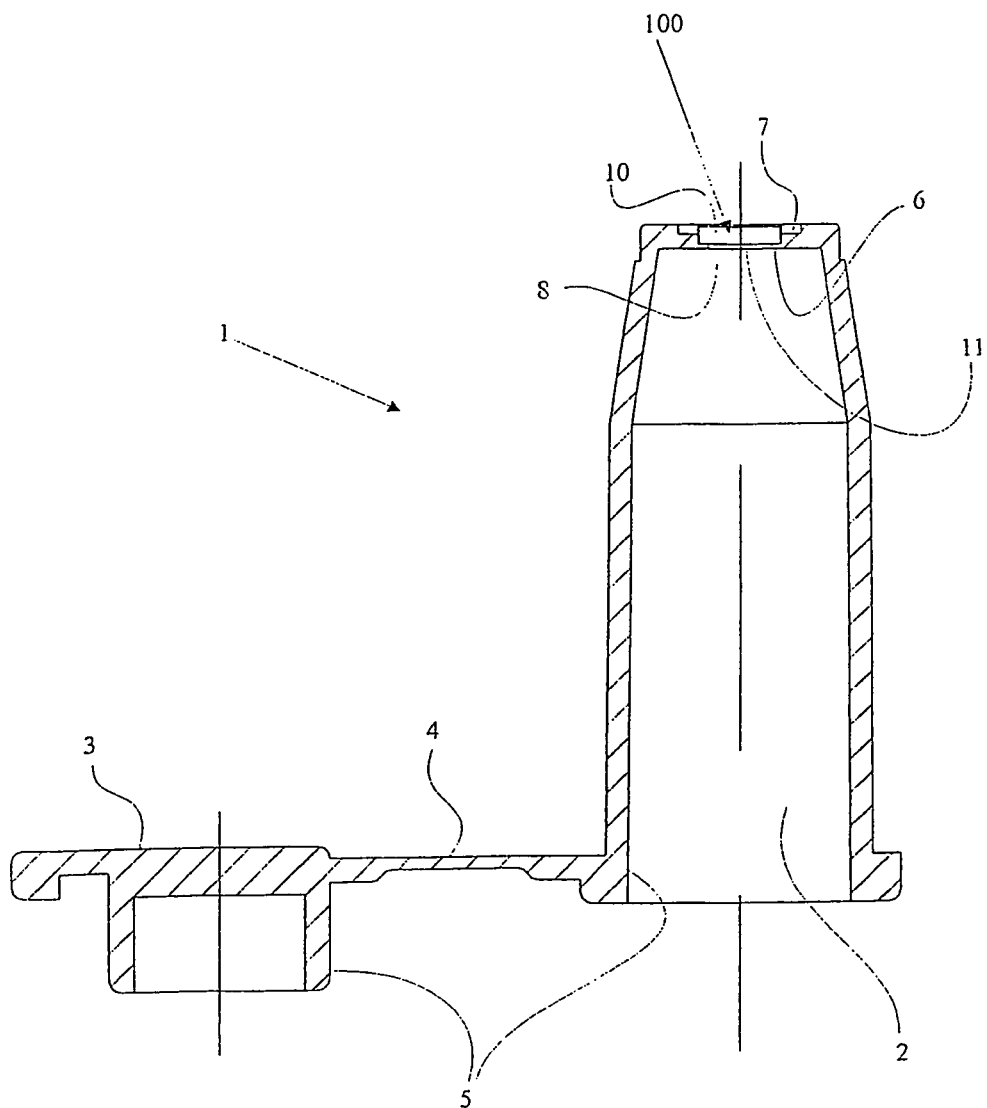
FIG. 1: An opening or a recess (8) is incorporated in the bottom of a reaction vessel (2) with a bearing surface (6) onto which the affinity matrix (100) can be placed from outside. The affinity matrix (100) is glued by spreading adhesive into an adhesive edge (7) provided for this purpose.

FIG. 19: Selected time series image (after an silver development time of 15 min) of the hybridisation of a biotin-labelled wild type PCR (exon ¾, KDL24) in the reaction vessel according to the invention. The layout of the chip is shown in FIG. 1.

Figure 20:
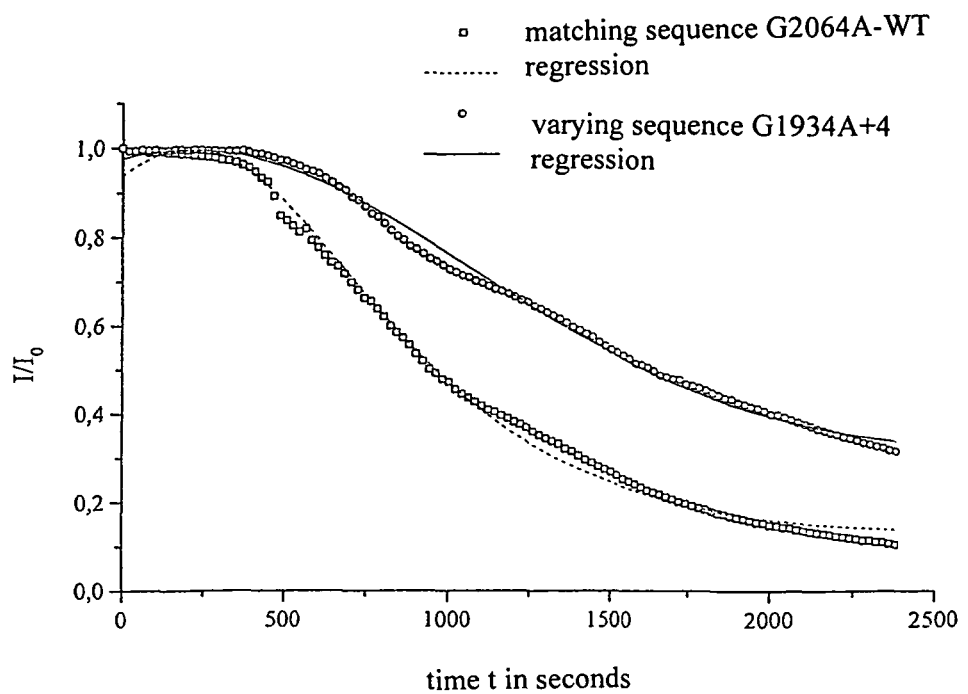

FIG. 20: Diagram of the time behaviour of the blackening of two spots by silver precipitation. One spot has the perfect complementary sequence of the target DNA (wild type G2064A-WT), the other differs by one base (mutation G1934A+4). The relevant regression functions are also plotted.

Figure 21:
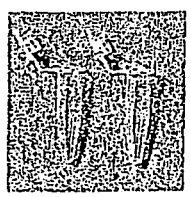

FIG. 21: Photographs of two standard reaction vessels made of polypropylene and having a filling volume of 1.5 ml.

DETAILED DESCRIPTION OF THE INVENTION

Laboratory reaction vessels having a typical shape and size are understood within the context of the present invention as reaction vessels which are usually used as single-use reaction vessels, containing 1.5 ml in the standard design, in especially biology or molecular biology laboratories. Such laboratory reaction vessels are also called tubes and after the most famous manufacturer, especially Eppendorf tubes or "Eppis" (Hamburg, Germany). Thus, laboratory reaction vessels having a typical shape and size are supplied by Eppendorf as standard reaction vessels or safe-lock reaction vessels. Of course, reaction vessels from manufacturers such as Greiner (Frickenhausen, Germany), Millipore (Eschbom, Germany), Heraeus (Hanau, Germany) and BIOplastics (Landgraaf, the Netherlands) as well as other manufacturers, having a shape and size such as is especially typical for laboratory reaction vessels from Eppendorf, can be used within the context of the present invention. Examples of laboratory reaction vessels having a typical shape and size are shown in FIG. 21.

Within the context of the present invention laboratory reaction vessels of typical shape and size are especially understood not as round-bottom flasks or other flasks such as Erlenmeyer flasks, beakers or measuring cylinders.

The reaction vessel according to the invention differs from the aforesaid reaction vessels in that a supporting element with probe molecules immobilised thereon on predetermined regions is arranged on one of its base surfaces. Such a supporting element with probe molecules immobilised thereon on predetermined regions is hereinafter also called a chip or affinity matrix. The predetermined regions on the support are hereinafter also called array elements.

Despite the modification of a conventional laboratory reaction vessel by incorporating such a chip, the reaction vessel has a typical shape and/or size for a laboratory reaction vessel. The reaction vessel according to the invention thus has a rotationally symmetrical shape, especially a cylindrical or substantially cylindrical shape. Of the typical shapes for conventional laboratory reaction vessels and thus feasible shapes for the reaction vessel according to the invention, a conical shape deviating from the cylindrical basic shape is also included, wherein the tapering preferably appears in the direction of the affinity matrix. Typical shapes are furthermore combinations of cylindrical or substantially cylindrical regions and conical regions (see FIGS. 1-4 and 21 among others). As a result of the typical shape and size for laboratory reaction vessels, the reaction vessel according to the invention is especially compatible with conventional table-top centrifuges such as those from manufacturers such as Eppendorf or Heraeus, i.e. the reaction vessel according to the invention is suitable for centrifugation in normal table-top centrifuges. Normal maximum outside diameters for standard laboratory reaction vessels and thus also for the reaction vessel according to the invention lie in the range from 0.8 cm to 2 cm, preferably 1.0 cm to 1.5 cm and especially preferably 1.1 cm to 1.3 cm. Further preferred outside diameters are up to 0.9 cm, up to 1.2 cm, up to 1.4 cm, up to 1.6 cm and up to 1.7 cm. The height of the reaction vessel is usually 1.5 cm to 5.0 cm, preferably 2.0 cm to 4.0 cm, especially preferably 2.5 cm to 3.5 cm and most preferably 2.8 cm to 3.2 cm. Further preferred heights are up to 2.6 cm, up to 2.7 cm, up to 2.9 cm, up to 3.0 cm, up to 3.1 cm, up to 3.3 cm and up to 3.4 cm. In special embodiments the height can also be 1.0 cm or more. The reaction vessel according to the invention can be centrifuged in normal table-top centrifuges and can thus be used for example in conventional table-top centrifuges such as a standard table-top centrifuge with a standard rotor from Eppendorf and also in normal racks and racks or holders for reaction vessels such as for example a tube rack from Eppendorf. Normal pipettes or syringes such as variable and fixed volume pipettes from Eppendorf for example can be used to insert the sample to be analysed and other reagents required to carry out the detection reaction into the reaction vessel.

The arrangement of the chip in the reaction vessel according to the invention makes it possible to detect the interaction reaction between target and probe molecules by usual methods such as fluorescence detection or radio-chemical methods for example. The application of absorption measurements has proved particularly advantageous, since this can be carried out especially cost-effective. Such an absorption measurement can be substantially improved and made more cost-effective by using a reactive staining method which takes place on the areas of the surfaces at which an interaction reaction has taken place. In this case, the precipitation of silver at target molecules labelled with gold nanospheres (see DE 100 33 334.6 and WO 02/02810) has proved especially effective. In order to detect the silver precipitation it is possible to use a device which uses one or a plurality of light-emitting diodes of arbitrary emission wavelength as light source and for example, has a CCD camera for spatially resolved detection of the interaction reaction on the predetermined regions of the chip.

The following definitions are used among others for the description of the present invention:

Within the context of the present invention a probe array is understood as an arrangement of molecular probes on a surface, wherein the position of each probe is separately determined. The array preferably comprises defined sites or predetermined regions, so-called array elements which are especially preferably arranged in a certain pattern, wherein each array element usually only contains one species of probes.

Within the context of the present invention a probe or a probe molecule is understood as a molecule which is used to detect other molecules by a specific, characteristic binding behaviour or a specific reactivity. For the probes arranged on the array it is possible to have any type of molecule, which can be coupled to solid surfaces and has a specific affinity. In a preferred embodiment this comprises biopolymers from the classes of peptides, proteins, nucleic acids and/or their analogues. The probes are especially preferably nucleic acids and/or nucleic acid analogues. Both DNA and also RNA molecules can be used as nucleic acids. For example, the oligonucleotide probes can comprise oligonucleotides having a length of 10 to 100 bases, preferably 15 to 50 bases and especially preferably 20 to 30 bases, which are immobilised on the array surface.

Within the context of the present invention a target or target molecule is understood as the molecule to be detected using a molecular probe. In a preferred embodiment of the present invention, the targets to be detected are nucleic acids. However, the probe array according to the invention can also be used to detect protein/probe interactions, antibody/probe interactions etc.

Within the context of the present invention an array element or a predetermined region is understood as an area on a surface defined for the deposition of a molecular probe; the sum of all occupied array elements is the probe array.

Within the context of the present invention a labelling denotes a detectable unit, for example a fluorophore or an anchor group to which a detectable unit can be coupled.

Within the context of the present invention a substrate is understood as a molecule or a combination of molecules present in dissolved form in the reaction medium which is precipitated locally with the aid of a catalyst or a crystallisation nucleus and/or a converting agent. The converting agent can for example be a reducing agent as in the precipitation of silver or an oxidising agent as in the production of a dye by enzymatic oxidation.

Within the context of the present invention a supporting element or support is understood as a solid body on which the probe array is constructed. The supporting element with the probes arranged thereon is hereinafter also designated as a chip and in special embodiments of the present invention can also comprise a base element on which the actual chip is arranged.

The supporting element can be arranged in the reaction vessel according to the invention, by simply inserting or clamping it into a laboratory reaction vessel, preferably by shaping the chip surface such that it can be inserted or clamped tightly in a laboratory reaction vessel, for example, in its lid. Alternatively, a base surface of the laboratory reaction vessel is flattened such that the supporting element can be attached thereon. Should this be necessary for technical reasons, the support or the chip can also be inserted in the side walls of the reaction vessel according to the invention.

In an advantageous embodiment, however, the base surface, preferably the bottom of the laboratory reaction vessel has a recess to receive the support. The support or chip can for example, be glued in and/or clamped in and/or screwed in and/or welded into this recess, especially by laser welding, and/or snapped in from inside and/or from outside. In these embodiments the reaction vessel according to the invention has a typical shape and size for a laboratory reaction vessel and an opening formed as an enclosure to receive affinity matrices, especially surface-bound substance libraries. Examples of such embodiments of the reaction vessel according to the invention are given in FIGS. 1 to 4. In addition to the variants shown there, further combinations of the type of fixing of the support are naturally feasible.

Mounting the support or the chip from inside has the advantage that even at higher internal pressure, for example, when using a centrifuge or when heating the sample liquid to temperatures near the boiling point, the support or the chip cannot be pressed outwards from its fixing in the reaction vessel. However, the mounting requires a higher effort than mounting from outside.

Clamping connections or threads or snap-in devices or devices for locking into place provide a frictional connection which is impermeable to liquid between reaction vessel and support or chip. Such variants combine the advantages of inserting the support or chip from inside into the reaction vessel with those of simplified assembly. A disadvantage here is a further connection point, e.g. the clamping connection and the higher number of components.

During the manufacture of the reaction vessel according to the invention, an injection-moulded standard laboratory reaction vessel especially from one of the aforesaid manufacturers will be usually taken as the starting point. This is cut at the bottom and then re-melted in a device especially designed for this purpose. Such a method is especially suitable for small numbers of items. For large numbers of items it is possible to injection-mould the reaction vessel directly in one of the aforesaid embodiments.

In order to protect the affinity matrix from dirt or contamination from outside, it is advantageous to stretch or stick a protection film on the underside of the reaction vessel, which is then removed from the reaction vessel shortly before use.

The base surface on which the supporting element is arranged with the probe molecules immobilised thereon on predetermined regions usually is the bottom of the reaction vessel according to the invention.

Alternatively, the support can also be attached in the lid of the reaction vessel. Mounting the supporting element or the chip surface in the lid of the reaction vessel is especially advantageous if the affinity matrix reacts sensitively to the conditions in one or a plurality of the reaction steps for the preparation and/or implementation of the detection reaction. These reaction steps can be carried out in this embodiment of the reaction vessel according to the invention in the upright reaction vessel, whereby the affinity matrix or the chip does not come in contact with the reaction and sample solutions and is thus protected. In order to carry out the detection reaction, the reaction vessel according to the invention is then turned or placed onto the lid so that the sample comes in contact with the surface-bound probes. In this way, the thermal and chemical loading of the affinity matrix or the chip is reduced.

The supporting element of the reaction vessel according to the invention is preferably optically transparent and/or non-fluorescent in the area of the detection surface. A detection surface is to be understood as the region of the supporting element, on which probe molecules are immobilised on pre-determined regions. In a preferred embodiment of the invention the probe molecules are deposited directly on the supporting element without the supporting element comprising another base element.

In other preferred embodiments the probe molecules are deposited on a preferably optically transparent and/or non-fluorescent chip which in turn is firmly connected to a base element which is preferably optically transparent and/or non-fluorescent in the detection region defined by the chip. The dimensions of the chip are smaller than the dimensions of the base element. In this case, the chip carrying the probe molecules and the base element together form the supporting element.

In a preferred embodiment of the reaction vessel according to the invention, the base surface opposite to the detection surface of the supporting element is likewise optically transparent and/or non-fluorescent in the region corresponding to the detection surface.

In general, a probe array according to the present invention comprises a support which allows the formation of arrays with probes on its surface. Such a support can be manufactured among others from materials selected from the group consisting of glass, filters, electronic apparatus, polymers, metallic materials and the like as well as arbitrary combinations of these materials.

The supporting element preferably consists of optically transparent and/or non-fluorescent materials. Such materials comprise for example glass, Borofloat 33 (for example obtainable from Schott, Jena, Germany), quartz glass, mono-crystalline $CaF_2$ (for example, obtainable from Schott), mono-crystalline silicon, phenylmethylmethacrylate and/or polycarbonate.

If the probe molecules are not applied directly to the supporting element but are applied to a chip, the chip likewise preferably consists of optically transparent and/or non-fluorescent materials. The materials especially comprise glass, Borofloat 33, quartz glass, mono-crystalline $CaF_2$, mono-crystalline silicon, phenylmethylmethacrylate and/or polycarbonate.

In addition to the optically transparent or non-fluorescent materials described hereinbefore for the supporting element or the chip, conventional filter, ceramic, metal, semimetal and/or plastic materials are also feasible. For example, nylon membranes specially manufactured for DNA libraries can be used as support materials.

The material of the container of the reaction vessel corresponds to the materials usually used for laboratory reaction vessels and is for example, selected from the group consisting of glass, glass ceramic, plastic-coated glass and plastics or organic polymers such as polypropylene, polyethylene, polystyrene, polycarbonate, PVC, polymethylmethacrylate, silicone plastic, rubber, polytetrafluorethylene and/or nylon. For special embodiments, metals, especially stainless steels, platinum and/or aluminium are also feasible as the material of choice.

The reaction vessel has a typical size for a laboratory reaction vessel. Typical filling volumes lie in the range of 100 µl to 2.5 ml, but can also be higher or lower in special embodiments. Especially preferably the reaction vessel has a normal filling volume for a standard Eppendorf tube of up to 1.5 ml. Further preferred filling volumes are up to 0.4 ml, up to 0.5 ml, up to 0.7 ml, up to 1.0 ml or up to 2.0 ml.

The immobilised probe molecules on the supporting element usually comprise a substance library. Within the context of the present invention a substance library is to be understood as a collection of different substances which are immobilised on a surface. The arrangement of the substances on the surface is made such that a specific uniquely identified site is assigned to each substance and each substance is immobilised completely separately from the others.

The substance libraries can comprise protein substance libraries, peptide substance libraries and nucleic acid substance libraries. Protein substance libraries can especially comprise antibody, receptor molecule and membrane protein libraries. Feasible peptide libraries are in particular receptor ligand libraries, pharmacologically active peptide libraries and peptide hormone libraries.

Nucleic acid substance libraries especially are DNA and RNA molecular libraries. In DNA molecular libraries ribosomal DNA sequences of micro-organisms can especially preferably be attached to the supporting element. Moreover, these can comprise nucleic acid substance libraries for SNP analysis. Also feasible are protein or nucleic acid substance libraries which allow a so-called "expression profiling". Another alternative is combinatorial substance libraries.

The substance libraries are applied to the supporting element such that they come in contact with the sample space of the reaction vessel. The supporting element of the reaction vessel is thus preferably characterised in that it has on its surface one detection surface with a substance library and is optically transparent at least in the detection region.

Another advantageous embodiment of the invention is that the reaction vessel formed is sealed and aqueous samples can be heated to temperatures of up to 100° C. for hours without this resulting in any escape of liquid or the samples evaporating. That is to say, the reaction vessels according to the invention can be used in wide ranges of temperature and are just as efficient when frozen in liquid nitrogen (at −196° C.) as in a boiling water bath. Equally, they are also suitable for withstanding autoclaving for 15 minutes at 121° C. for example. Moreover, the reaction vessels according to the invention are preferably also chemically resistant to acids, bases and organic solvents such as alcohol, acetone or phenol.

The reaction vessel according to the invention preferably is provided with the caps or cap locks usually used in laboratory reaction vessels such as, for example, the systems Easy-to-Open (Biozyme, Oldendorf, Germany), Safe-Lock (Eppendorf) and the like. In this way, it is ensured that the reaction vessel is sealed and is easy to open, especially with one hand.

If the supporting element is inserted in a recess of the reaction vessel, sufficient sealing of the reaction vessel is usually achieved by sticking and/or clamping the supporting element into the recess and if necessary, then applying a sealing material to the required regions.

The adhesives are usually applied using commercially available dispensers. Possible adhesives are preferably platinum cross-linking polydimethylsiloxanes such as Sylgard 182 or Sylgard 184 (Dow Corning, Midland, Mich., USA). Alternatively other adhesives such as silicone adhesives, polyurethane adhesives, epoxy resin adhesives, cyanacrylate adhesives, acrylic adhesives and/or heat adhesives can be used. Various rubbers such as silicone rubber and/or rubber materials and the like can be used as sealing materials.

The supporting element arranged in the reaction vessel is preferably a so-called DNA chip. Such a DNA chip comprises for example a DNA library bound on a glass surface with unique allocation of the DNA sequences to predetermined regions of the surface.

Within the context of the present invention the probe arrays with probes immobilised at defined sites used can generally be manufactured using conventionally known methods. DNA chips are preferably produced by generally common spotting methods or by special spatially resolved synthesis methods. Alternative methods such as synthesis methods using a light-guided DNA synthesis can also be considered for the manufacture. Methods for manufacturing probe arrays or chips, especially DNA chips are known to the person skilled in the art and are described among others in DE 197 06 570, EP 0 969 918 and WO 98/36827.

The probe arrays are preferably manufactured alternatively according to two fundamentally different methods.

In one method, separately synthesised probes, for example oligonucleotides are deposited on surfaces using automatic machines, so-called spotters which ensure the spatially specific deposition of extremely small quantities of liquid, and are covalently or non-covalently linked to this. The method operates serially. Each spot is individually equipped with the probe.

Alternatively, probe arrays are produced by site-specific in situ synthesis of the probes, for example, of the oligonucleotide probes. The synthesis takes place in parallel, for example on the wafer scale. Suitable reagents for activating the array surface or suitable protective groups for synthesis of the probes on the array surface are known to the person skilled in the art.

The immobilisation of molecules on the array surface can take place either specifically or non-specifically. Specific immobilisation requires a selectivity of the interaction of certain chemical functions of the molecule to be immobilised with the surface of the substrate. An example of a specific, non-covalent immobilisation is the binding of biotin-labelled nucleic acid to a streptavidin-coated substrate. Amino-modified nucleic acids can be specifically immobilised via the reaction of the amino group with an epoxide, a carboxy function or an aldehyde. The immobilisation is preferably carried out via a terminal phosphate group of the probe or the monomer building block of a biopolymer probe on an aminated surface.

The site-specific immobilisation takes place via a plurality of mechanisms and chemical functions and can be both covalent and non-covalent. An example of this is the immobilisation of nucleic acids on a poly-L-lysine-modified substrate surface but also the immobilisation of chemically non-modified nucleic acids on epoxidized, aminated substrate surfaces or substrate surfaces occupied with aldehyde functions.

Methods likewise known to the person skilled in the art can also be used to deposit small quantities of material at predetermined sites on a substrate to manufacture a probe array which is inserted in the reaction vessel according to the invention. A number of such methods are described for example in D. J. Lockhart, E. A. Winzeler; Genomics, gene expression and DNA arrays; *Nature*, 405, pages 827-836, 2000.

Special embodiments of the reaction vessel according to the invention are described in detail hereinafter with reference to the drawings.

The reaction vessel (1) in FIG. 1 has substantially the dimensions of the usual reaction vessels on the market and preferably resembles a 1.5 ml standard reaction vessel made of polypropylene such as is manufactured in large quantities. It has an opening (8, 10) (within the context of the present invention also designated as recess) which is provided with a holding device into which the affinity matrix (100) can be inserted. The holding device generally comprises a bearing surface (6, 11) for the affinity matrix (100), a liquid opening (8) so that the surface-bound substance library (102) can be brought in contact with the sample, and a viewing opening (10) to allow the detection of transmitted light. Furthermore, the opening (8, 10) can be provided with an adhesive edge (7, 9) to simplify the bonding of the affinity matrix in the reaction vessel (2). In order that the affinity matrix (100) need not be stuck into the reaction vessel, special quick-acting closures can be provided. In this case, the sealing effect can be achieved by seals. The reaction vessel can be closed by a lid (3).

The affinity matrix (100) incorporated into the holder can be located at various positions in the reaction vessel (2). Thus, it is possible to affix the affinity matrices on the bottom of the reaction vessel, as shown in FIGS. 1 to 4. In this case, the affinity matrix (100) is always exposed to the sample substances.

Should the affinity matrix (100) react sensitively to one or a plurality of process steps, the matrix can also be mounted in the lid (3). The necessary conditioning steps of the sample are then carried out with the reaction vessel (1) standing upright, wherein the affinity matrix does not come in contact with the sample and is thus protected. For the detection reaction the reaction vessel is then turned upside down so that the sample comes in contact with the surface-bound substance library (102). This would reduce the thermal and chemical loadings of the affinity matrix (100).

The affinity matrices (100) can be connected to the reaction vessel (2) in various ways. In the variant shown in FIG. 1, the affinity matrix is placed from outside in a liquid opening (8) onto a support (6). Adhesive is placed in an adhesive edge (7) which encloses the affinity matrix (100) due to flow and capillary action and connects to the reaction vessel (2) in a liquid-sealed and temperature-stable fashion. Alternatively, the affinity matrix (100) can also be welded to the reaction vessel (2), for example, by laser welding. The affinity matrix (100) is thus mounted into the reaction vessel such that the surface-bound substance library (102) can come in contact with the sample solution. After installing the affinity matrix (100), it is possible to make optical transmitted-light detection using the readers (1000) as shown in FIGS. 5 to 15.

Figure 2:
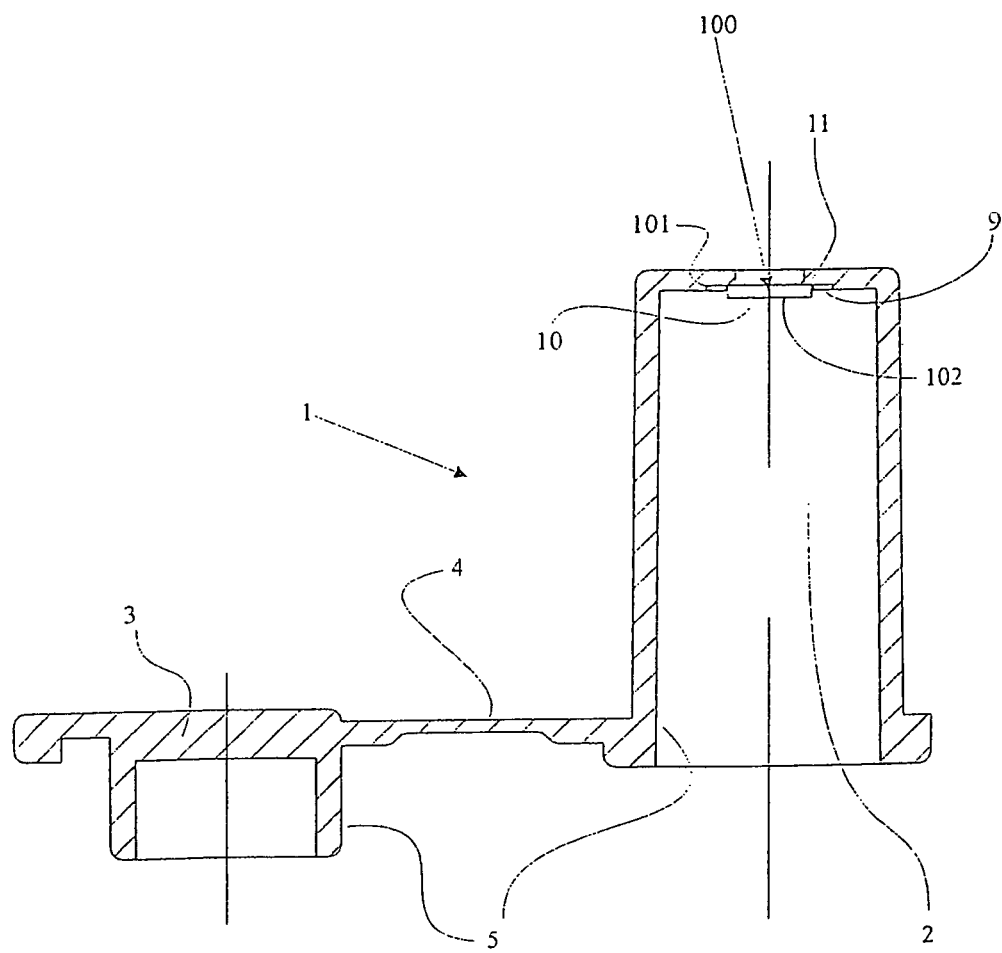
FIG. 2: An opening (10) is incorporated into the bottom of a reaction vessel (2) with a bearing surface (10) onto which the affinity matrix (100) can be placed from inside. The affinity matrix (100) is glued by spreading adhesive into an adhesive edge (9) provided for this purpose.

Alternatively, the affinity matrix (100) can also be mounted from inside as shown in FIG. 2. In this variant the bearing surface and the adhesive edge lie in the reaction space of the reaction vessel. This has the advantage that even at higher internal pressure, for example when used in a centrifuge or when heating the sample liquid to temperatures near the boiling point in the reaction space the affinity matrix (100) cannot be pressed out of its holder. However, the mounting requires a higher effort.

Figure 3:
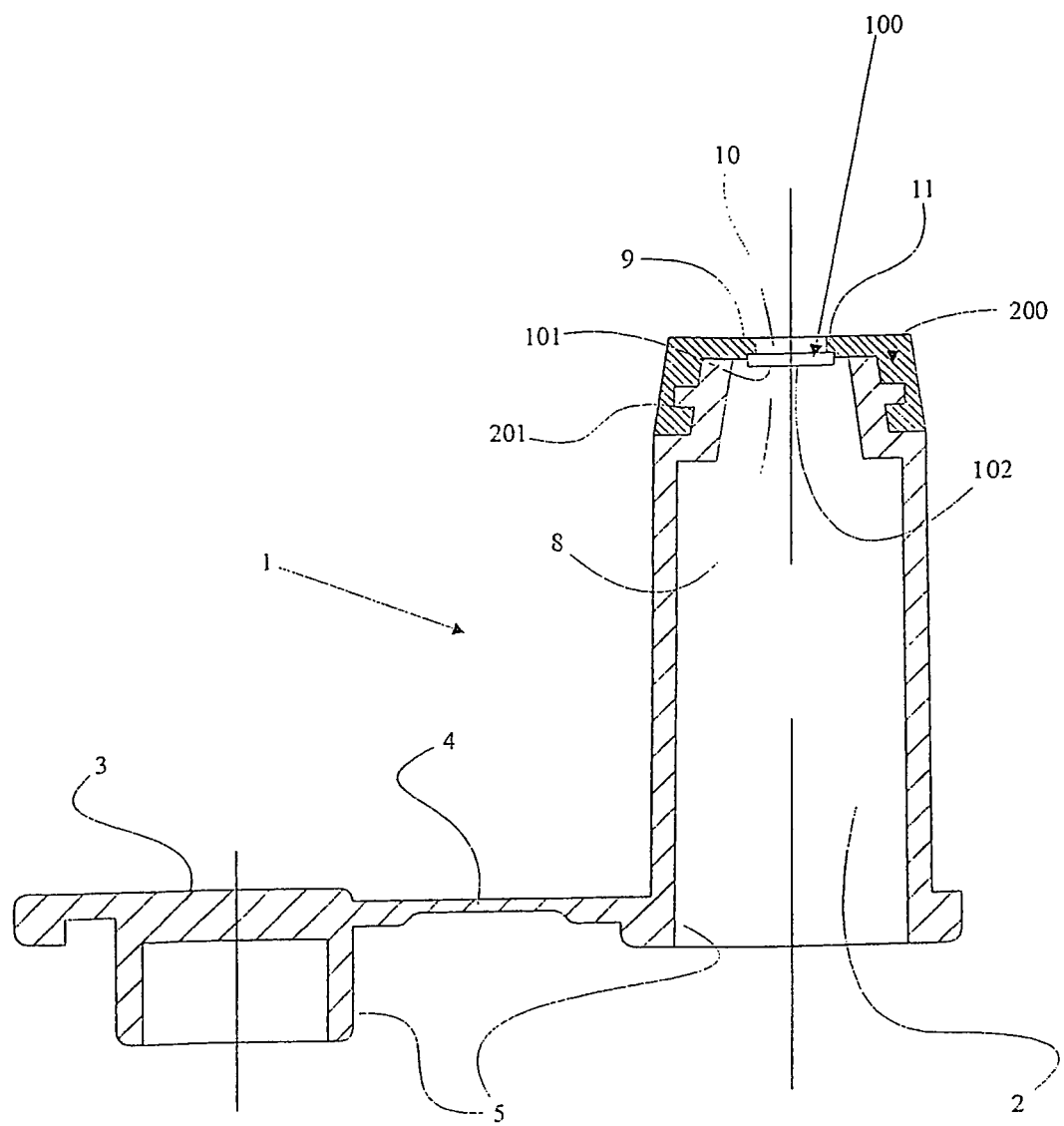
FIG. 3: The bottom of a reaction vessel (2) is provided with a clamping connection (201). A chip support (200) can be pressed in a liquid-sealed fashion onto this clamping connection (201). The chip support has an opening (10) in which the affinity matrix (100) can be placed on a bearing surface provided therefore and then glued.

FIG. 3 shows a variant in which the affinity matrix (100) is mounted in a chip support. The chip support (200) is then pressed onto the reaction vessel (2). A clamping connection or a thread (201) provides a frictional and liquid-impermeable connection between reaction vessel (2) and chip support (200). This variant combines the advantages of an affinity matrix (100) inserted into the reaction vessel from inside with those of simplified assembly. A disadvantage is another connection point such as the clamping connection for example and the higher number of components.

Figure 4:
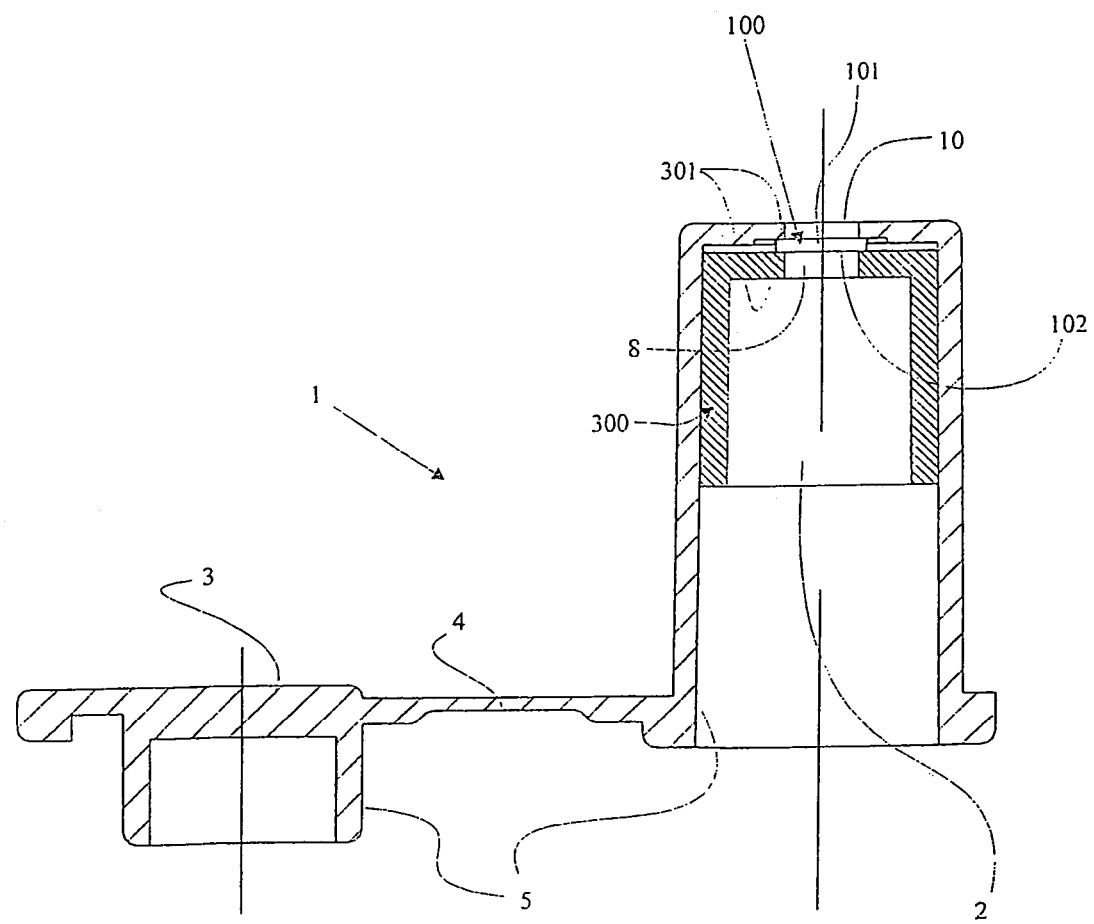
FIG. 4: In the embodiment shown in FIG. 4 the affinity matrix (100) is clamped in a liquid-sealed fashion between the reaction vessel (2) and a clamping sleeve (300) so that gluing is not absolutely necessary.

FIG. 4 shows a variant in which the affinity matrix (100) is clamped by means of a clamping sleeve (300) inserted from inside between reaction vessel (2) and clamping sleeve (300) such that a bonding of the affinity matrix (100) to the reaction vessel (2) becomes superfluous. However, this design requires a very high manufacturing precision for the clamping sleeve (300) and reaction vessel (2) to ensure liquid-sealed clamping of the affinity matrix (100). In a further variant the clamping sleeve (300) can be screwed into the reaction vessel (2).

In a further aspect of the present invention a method is provided for detecting the specific interaction between molecular target and probe molecules which comprises the following steps:
 a) Providing a reaction vessel according to the invention described hereinbefore;
 b) Interacting the target with the probes arranged on predetermined regions (array elements); and
 c) Detecting the interaction.

The targets to be analysed can be present in any type of sample, preferably in a biological sample. Prior to their detection and quantification by the method according to the invention the targets are preferably isolated, purified, copied and/or amplified.

The amplification usually takes place by conventional PCR methods. The amplification is preferably carried out as multiplex PCR in a two-stage process (see also WO 97/45559). In a first stage a multiplex PCR is carried out by using fusion primers whose 3' ends are gene-specific and whose 5' ends represent a universal region. The latter is the same for all forward and reverse primers used in the multiplex reaction. In this first stage the primer quantity is limiting. As a result, all multiplex products can be amplified to a standard molar level provided that the number of cycles is sufficient to achieve primer limitation for all products. In a second stage universal primers which are identical to the 5' regions of the fusion primers are added. Amplification takes place as far as the desired quantity of DNA is obtained.

In the method according to the invention detection is preferably accomplished by providing the bound targets with at least one labelling which is detected in step c).

In an alternative embodiment the probe molecules arranged on the probe array, which serve to detect the molecular interactions with the target molecules, comprise at least one labelling and at least one predetermined cleavage site, i.e. a labile or selectively cleavable bond which can be specifically destabilised or cleaved. The selectively cleavable bond arranged between the labelling and the position of the linkage of the probes to the array surface makes it possible for the labelling or detectable unit to be used for specific detection of the molecular interaction between probes and targets. In this case, the predetermined cleavage site or selectively cleavable bond is positioned within the probe molecule so that breaking of the bond results in detachment of the detectable unit or the anchor group with the detectable unit from the array surface. On the other hand, those labellings whose probe molecules have interacted specifically with target molecules remain linked to the array surface since the cleavage product of the probe linked to the labelling or the probe fragment remains coupled via the interaction with the target with the second cleavage product of the probe which is immobilised on the surface of the array. The preparation of such probe molecules comprising at least one predetermined cleavage site is described in detail in the German Patent Application DE 101 42 643.7.

In this embodiment the selectively cleavable bonds are preferably provided such that they are also effectively cleavable when the probes are immobilised on the array surface. The selectively cleavable bond can preferably be selectively cleaved by chemical and/or physical methods. An efficient cleavage at the surface is especially ensured by agents having small dimensions such as atoms and ions. The labile bond is thus preferably selectively cleavable by simple chemical agents, for example, by adding ions, especially preferably acid anions, base cations, fluoride and/or heavy metal ions such as mercury and/or silver ions.

In cases where the array is manufactured by immobilising separately synthesised oligonucleotides, the selectively cleavable bond is stable under the conditions used during immobilisation of the probes on the array surface. If the probes are manufactured in situ by site-specific synthesis on the array surface, it is preferred that the labile bond can be produced efficiently as part of the synthesis procedure. It is especially preferable if the labile bond can be prepared using phosphoramidite chemistry. The same also applies to the installation of the detectable unit.

Consequently it is preferred that the selectively cleavable bond is present in a nucleic acid which can be produced by conventional DNA or RNA synthesis. Especially preferably the probe molecules of the probe array according to the invention comprise a nucleic acid having the formula $A_1$-S-$A_2$, wherein S is a nucleic acid or a nucleotide building block which comprises at least one selectively cleavable bond, and $A_1$ and $A_2$ are arbitrary nucleic acids or nucleic acid analogues. The probe molecule is immobilised on the surface of the probe array according to the invention via one of the two nucleic acids or nucleic acid analogues $A_1$ and $A_2$ whilst the other has at least one labelling. S is preferably a nucleotide dimer, which is bridged by a selectively cleavable bond.

Examples of especially preferred DNA nucleotide building blocks S, which comprise a selectively cleavable bond, are given in the following formula I:

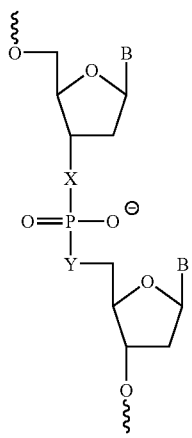

I

In this case, X and Y can be selected independently of one another from the group preferably consisting of O, NH and S, where X and Y are not simultaneously O.

B stands for a nucleo base such as the purine derivatives adenine and guanine and the pyrimidines cytosine and thymine.

The selectively cleavable bond within the nucleotide sequence of such oligonucleotide probes is preferably a phosphothioate bond or a phosphoramidate bond. Especially preferably the phosphothioate bond, i.e. a sugar-O—P—S-sugar bond replaces a phosphodiester bond, i.e. a sugar-O—P—O-sugar bond of an unmodified oligonucleotide. In this embodiment two nucleosides are linked by a phosphothioate bond.

Alternatively the selectively cleavable bond within the nucleotide sequence can also be another sulphur or nitrogen-modified ester bond such as, for example, a phosphonothioate bond.

Further examples for the preparation of selectively cleavable bonds in the probe molecules of the probe array according to the invention are amide, 1,2-diol, disulphide and/or sulphonyl groups as well as other groups which are described in U.S. Pat. No. 5,118,605 and which are cleavable under the conditions specified therein. However, these groups are less preferred since among other things these cannot be incorporated in oligonucleotide probes using conventional nucleic acid synthesis.

Alternatively, physical methods can also be used for cleaving the selectively cleavable bond in the probe molecules. Thus, for example, the selectively cleavable bond can be selectively cleaved photolytically. Nucleotide building blocks which comprise a photolytically selectively cleavable bond and which can be used for synthesis of the probe molecules of the probe array according to the invention are described for example in U.S. Pat. No. 5,367,066, U.S. Pat. No. 5,552,538 and U.S. Pat. No. 5,578,717.

Further examples of especially preferred RNA nucleotide building blocks which comprise a chemically or physically selectively cleavable bond are given in the following formula II:

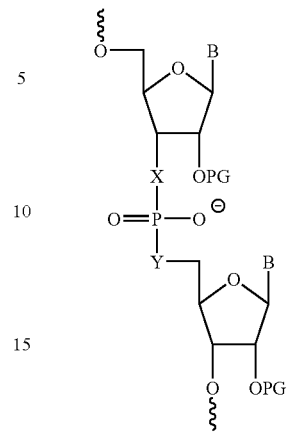

II

Here X and Y can be selected independently of one another from the group preferably consisting of O, NH and S, where X and Y are not simultaneously O, if PG is not a labile protective group.

PG is preferably selected from the group consisting of H and labile protective groups such as

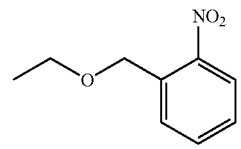

(photolabile) or

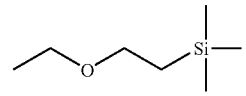

(labile e.g. towards fluorine ions).

B in formula II stands for a nucleo base such as the purine derivatives adenine and guanine as well as the pyrimidines cytosine and uracil.

Preferred however are probe molecules with selectively cleavable bonds which are stable under normal atmospheric, temperature and light conditions.

In an alternative embodiment the labile bond is selectively cleavable by enzymatic methods. Examples of nucleotide building blocks comprising such labile bonds are described in U.S. Pat. No. 4,775,619 and U.S. Pat. No. 4,876,187. However, enzymatic methods for cleaving the selectively cleavable bond are less preferred within the context of the present invention, since enzymatic activities are severely hindered by the proximity of the selectively cleavable bond to the surface as a result of the immobilisation of the probe molecules. Consequently, an enzymatic cleavage reaction has only a very low efficiency, which results in an undesired high signal background by falsely positive measurement results. Thus, in a preferred embodiment of the probe array according to the invention the selectively cleavable bond cannot be selectively cleaved by enzymatic methods.

In another preferred embodiment of the probe array according to the invention, the selectively cleavable bond is located approximately in the centre between the immobilisation site of the probe on the array surface and the position of the probe labelling. It is thus ensured that the probability of interaction of the target with the immobilised probe fragment which corresponds to the residue of the probe remaining on the surface after the bond cleavage, is substantially reduced or almost impossible. On the other hand, if the selectively cleavable bond is located too close to the array surface, the complex of probe and target molecules after the cleavage is thus no longer sufficiently stabilised since the hybridisation of the target with the probe fragment immobilised on the array surface is not sufficiently stable. This would result in falsely negative measurement results.

As has already been mentioned, the labelling coupled to the targets or probes is preferably a detectable unit or a detectable unit coupled to the targets or probes via an anchor group. The method according to the invention is extremely flexible with regard to the possibilities for detection or labelling. Thus, the method according to the invention is compatible with a plurality of physical, chemical or biochemical detection methods. The only requirement is that the unit or structure to be detected is coupled directly to a probe or a target, for example, an oligonucleotide or can be linked via an anchor group which can be coupled to the oligonucleotide.

The detection of the labelling can be based on fluorescence, magnetism, charge, mass, affinity, enzymatic activity, reactivity, a gold marker and the like. For example, the labelling can be based on using fluorophore-labelled structures or building blocks. In connection with fluorescence detection, the labelling can be an arbitrary dye which can be coupled to targets or probes during or after their synthesis. Examples therefore are Cy dyes (Amersham Pharmacia Biotech, Uppsala, Sweden), Alexa dyes, Texas red, fluorescein, rhodamine (Molecular Probes, Eugene, Oreg., USA), lanthanides such as samarium, ytterbium and europium (EG&G, Wallac, Freiburg, Germany).

In addition to fluorescence markers also luminescence markers, metal markers, enzyme markers, radioactive markers and/or polymer markers can be used as marker or as detection unit which is coupled to the targets or probes.

Equally, a nucleic acid can also be used as a marker (tag) which can be detected by hybridisation with a tagged reporter (sandwich hybridisation). Various molecular-biological detection reactions such as primer extension, ligation and RCA can be used to detect the tag.

In an alternative embodiment of the method according to the invention, the detectable unit is coupled to the targets or probes via an anchor group. Preferably used anchor groups are biotin, digoxygenin and the like. The anchor groups are converted in a subsequent reaction with specifically binding components, for example, streptavidin conjugates or antibody conjugates which are themselves detectable or trigger a detectable reaction. When using anchor groups, the conversion of the anchor groups into detectable units can take place before, during or after adding the sample comprising the targets or if necessary before, during or after the cleavage of the selectively cleavable bond in the probes.

The tagging or labelling can also takes place according to the invention by interaction of a tagged molecule with the probe molecules. For example, tagging can take place by hybridisation of one of the oligonucleotides tagged as described previously with one oligonucleotide probe or an oligonucleotide target.

Further tagging methods and detection systems suitable within the context of the present invention are described for example in Lottspeich and Zorbas, Bioanalytik, Spektrum Akademischer Verlag, Heidelberg, Berlin, 1998, Chapter 23.3 and 23.4.

In a preferred embodiment of the method according to the invention, detection methods are used which yield as a result an adduct with a certain solubility product which results in precipitation. Substrates which can be converted into a barely soluble, usually stained product are especially used for tagging. For example, enzymes, which catalyse the conversion of a substrate into a barely soluble product, can be used for this tagging reaction. A series of possible reactions which are suitable for resulting in a precipitation on array elements as well as possibilities for detecting the precipitate are described for example in the International Patent Application WO 00/72018 and in the International Patent Application WO 02/02810 to which content reference is hereby expressly made.

In an especially preferred embodiment of the method according to the invention the bound targets are provided with a tag which catalyses the reaction of a soluble substrate to form a barely soluble precipitate on the array element on which a probe/target interaction has taken place or which acts as a crystallisation nucleus for the conversion of a soluble substrate into a barely soluble precipitate on the array element on which a probe/target interaction has taken place.

In this way the use of the method according to the invention thus allows the simultaneous qualitative and quantitative analysis of a plurality of probe/target interactions wherein individual array elements having a size of $\leq 1000$ μm, preferably of $\leq 100$ μm and especially preferably of $\leq 50$ μm can be achieved.

The use of enzymatic markers is known in immune cytochemistry and in immunological microtitre plate-based tests (see E. Lidell and I. Weeks, Antibody Technology, BIOS Scientific Publishers Limited, 1995). Thus, for example, enzymes catalyse the conversion of a substrate into a barely soluble, generally stained product.

Another possibility for the detection of molecular interactions on arrays involves the use of metal tags. In this case, for example, colloidal gold or defined gold clusters are coupled with a target, if necessary via certain mediator molecules such as streptavidin. The staining produced by the gold tagging is preferably intensified by subsequent reaction with baser metals such as silver, wherein the gold tag coupled to the target acts as a crystallisation nucleus or catalyst, for example, for the reduction of silver ions to form a silver precipitate. The targets coupled to gold tags are hereinafter also called gold conjugates.

In this embodiment of the method according to the invention the probe/target interaction can be relatively quantified. The relative quantification of the concentration of bound targets on a probe array is made by detecting a precipitate or a deposit via the concentration of tags coupled to the targets which catalyse the reaction of a soluble substrate to form a barely soluble precipitate on the array element on which a probe/target interaction has taken place or which act as a crystallisation nucleus for such reactions. For example, in the case of HPLC-purified oligonucleotide probes tagged with nanogold, the ratio of bound target to gold particles is 1:1. In other embodiments of the present invention this can be a multiple or also a fraction thereof.

In this embodiment of the detection method according to the invention, detection is carried out by measuring the transmitted-light absorption or incident-light reflection caused by the precipitate which is produced on the array elements on which a probe/target interaction has taken place, by the catalytic action of the labelling coupled to the bound target.

In cases where colloidal gold or defined gold clusters are coupled to the targets, the light absorption is caused by the presence of these metal labellings. In order to intensify the light absorption, however, a non-transparent precipitate is preferably deposited catalytically by such interaction hybrids, i.e., the targets provided with a labelling such as colloidal gold or defined gold clusters for example. The use of silver as a precipitate has been found to be especially advantageous in the case of gold conjugates.

The qualitative and/or quantitative detection of the probe/target interaction by measuring the transmitted light absorption is explained hereinafter with reference to an example. Naturally, the procedure described hereinafter is not restricted to the silver/gold staining described hereinbefore but can also be suitably applied to all detection methods in which the bound targets are provided with a labelling which catalyses the reaction of a soluble substrate to form a barely soluble precipitate on the array element on which a probe/target interaction has taken place or which acts as a crystallisation nucleus for the conversion of a soluble substrate into a barely soluble precipitate on the array element on which a probe/target interaction has taken place.

The target molecule is first biotinylated, e.g. using PCR. The PCR product is hybridised against a substance library (102), for example a DNA library. Streptavidin-functionalised gold beads were then added to the reaction vessel (1) according to the invention, which react with the biotinylated hybrids, for example DNA hybrids. A silver precipitate can be produced on the gold beads now specifically bound to the surface, by for example reducing silver nitrate with hydroquinone under the catalytic action of gold (see among others WO 00/72018, DE 100 33 334.6, M. A. Hayat, Immunogold-Silver Staining, CRC Press, New York, 1995).

The absorption of light by the silver precipitate depends on the quantity of precipitated silver. Consequently, the light intensity I that radiates the precipitate can be calculated using a function similar to the Lambert-Beer Law:

$$I = I_0 * \exp(-a*b) \quad (I)$$

Here I is the light intensity after absorption, $I_0$ is the light intensity before absorption, a is an absorption coefficient multiplied by the shadowing per unit area b by the silver precipitate. The intensity I and the time t are available as measured quantities. These measured quantities are obtained by illuminating the supporting element with the substance library and recording the transmitted light using a camera (see FIG. 19). This recording is repeated at regular intervals whilst the silver precipitation is carried out. The brightness values of the individual library regions (spots) are evaluated for each recording, whereby the intensity I of each spot is obtained. The brightness values can be calculated automatically using standard software, such as for example IconoClust® (Clondiag, Jena, Germany). The measurement curves depicted in FIG. 20 are obtained by plotting $I/I_0$ as a function of the time t. The Lambert-Beer Law as given by equation (I) can be connected with the silver precipitation time series thus obtained as follows.

The area F shaded by a silver bead is:

$$F = \pi * r^2 \quad (II)$$

Since the precipitation rate per surface element can be regarded as constant for a spot, the radius r of the silver beads also increases at a constant rate:

$$r = dr/dt * t \quad (III)$$

The shading per unit of area b by the silver precipitate is proportional to the number of silver beads per unit of area N, the shading area per silver bead F and a constant k.

$$b = N*F*k \quad (III)$$

The function for the intensity I as a function of the time t is thus calculated as $$I = I_0 * \exp(a'*t^2), \quad (IV)$$

wherein a' is an unknown composite silver absorption constant.

For each silver precipitation reaction an individual precipitation rate must be assumed, so also for the unspecific reaction on the surface:

$$I = I_0 * \exp(-a'_H * t^2), \quad (V)$$

wherein $a'_H$ is the unspecific silver absorption constant.

Thus, at each spot i, a specific precipitation reaction and also an unspecific precipitation reaction takes place:

$$I_i = I_{0i} * (\exp(-a'_i * t^2) + \exp(-a'_H * t^2)) + O_i, \quad (VI)$$

where O is an equipment-dependent offset value.

The number of gold beads precipitated per unit of area depends on the one hand on the quantity of targets labelled with the gold beads and on the other hand on the binding strength of the targets, for example of the target DNA with the probes, for example, the spot DNA. If there is no target in the sample which interacts with a probe on the corresponding array element, no gold beads will be precipitated on the surface of this array element or spot. If the bond between the probe and target is weak, only very few gold beads will deposit on the surface of this array element.

Since b and therefore a' is directly proportional to the number N of gold beads and thus the number N of silver beads, a' is a measure for the concentration of target DNA and the binding strength of the target DNA on the array element or spot i.

FIG. 20 shows the silver precipitation time series of two spots which are hybridised against target DNA. The DNA probes of the spots differ by one base so that the target DNA is perfectly complementary to the probe of one spot, whilst it has a mismatch to the probe of the other spot. The silver absorption constant a' can be calculated from both measurement curves by nonlinear regression using equation (VI). In the case of a perfect match this is $2.566 \times 10^{-6}$ sec$^{-2}$ and in the case of a mismatch $4.83 \times 10^{-7}$ sec$^{-2}$ (see also Example 2). The two constants thus differ by almost one power of ten. Thus, the calculation of the constant a' can be used as a significant measured quantity for the binding strength and the concentration of target DNA on a spot. Furthermore, the time constant τ of the precipitation reaction can be determined from the constant a':

$$\tau = (1/a'_i)^{0.5} \quad (VII)$$

As a result of the regression, $I_0$ and O can be determined as further parameters. Illumination inhomogeneities of the DNA libraries can be corrected using the light intensity $I_0$. Alternatively, a flat field correction of all further images recorded for the time series at a later time point can be made using the image of the entire DNA libraries at time t=0. The validity of a measurement can be estimated using the parameter O.

Since the correct matching of an exponential function to the measured values requires a nonlinear regression algorithm (H. R. Schwarz, Numerische Mathematik, Teubner Verlag, Stuttgart, Deutschland, 1998), it can be advantageous to use a less accurate but more robust and therefore linear method for determining the measured values from the time series. For this purpose, the time values are squared and logarithms are taken of the measured intensity values. The values thus obtained are then fitted to a first-order linear equation. The regression parameters thereby obtained can be used as measured values and for testing the validity. Illumination inhomogeneities can no longer be corrected using a linear method in terms of $I_0$ but it is still possible to use a flat field correction.

A further variant of the evaluation consists in using the grey values of the individual spots directly as measured values after a predetermined time. However, this method has the disadvantages that it cannot be assessed in advance which time is optimal for the evaluation and that the measured values have a lower statistical reliability. In addition, any illumination inhomogeneity can only be carried out via a flat field correction.

In a further preferred embodiment of the method according to the invention, in step c) the time profile of the precipitate formation on the array elements is thus detected in the form of signal intensities. In this way, an exact determination of the relative quantitative amount of bound target can be ensured. Such a procedure is described in detail in the International Patent Application WO 02/02810.

As has already been mentioned, the targets are preferably provided with labellings which catalyse the reaction of a soluble substrate to form a barely soluble precipitate on the array element on which a probe/target interaction has taken place or which act as a crystallisation nucleus for such reactions.

In one embodiment of the present invention the targets can be provided directly with such tags.

Alternatively a direct tagging of the targets is dispensed with and the tagging is carried out via sandwich hybridisation or sandwich reactions with the probe interacting with the target and a tagged compound. Examples for such a procedure are:

Sandwich hybridisation with a tagged oligonucleotide complementary to the target sequence.

Sandwich hybridisation of tagged oligonucleotides hybridising in chain form with the target sequence; tagged oligonucleotides hybridising in chain form with the target sequence are understood within the context of the present invention as a set of tagged oligonucleotides of which at least one is complementary both to the target sequence and also to another oligonucleotide. The other oligonucleotides are self-complementary or complementary to one another so that during the hybridisation a chain of tagged oligonucleotides bound to the target sequence is formed.

Sandwich hybridisation with an oligonucleotide complementary to the target sequence which is coupled to a multiply tagged structure, for example, a dendrimer, described for example in WO 99/10362.

Another preferred possibility for coupling the targets to a tag involves the synthetic or enzymatic addition of a homopolymeric region, for example, a poly-A sequence to the targets, forming a continuous sequence, as is described for example in U.S. Pat. No. 6,103,474. In this embodiment the tagging is preferably carried out via sandwich hybridisation using a tagged oligonucleotide complementary to the homopolymer sequence with the variations described previously.

In another preferred embodiment of the present invention, signal amplification is carried out by amplification of parts of the homopolymer sequence added to the targets with the simultaneous incorporation of tagged bases, especially preferably via an RCA mechanism using a circular single-stranded template which shows complementarity to the homopolymer sequence.

Without claiming to be complete, the following Table 1 gives an overview of a number of possible reactions which are suitable for resulting in a precipitate on array elements on which an interaction between target and probe has taken place:

TABLE 1

| Catalyst or crystallisation nucleus | Substrate |
| --- | --- |
| Horseradish peroxidase | DAB (3,3'-diaminobenzidine) |
|  | 4-CN (4-chlor-1-naphthol) |
|  | AEC (3-amino-9-ethylcarbazole) |
|  | HYR (p-phenylene diamine-HCl and pyrocatechol) |
|  | TMB (3,3',5,5'-tetramethylbenzidine) |
|  | Naphthol/pyronine |
| Alkaline phosphatase | Bromochlorindoyl phosphate (BCIP) and nitrotetrazolium blue (NBT) |
| Glucose oxidase | t-NBT and m-PMS (nitrotetrazolium blue chloride and phenazine methosulphate |
| Gold particles | Silver nitrate |
|  | Silver tartrate |

The labelling of biological samples with enzymes or gold, especially nanocrystalline gold is sufficiently described (see among others F. Lottspeich and H. Zorbas, Bioanalytik, Spektrum Akademischer Verlag, Heidelberg, Berlin, 1998; E. Lidell and I. Weeks, Antibody Technology, BIOS Scientific Publishers Limited, 1995).

Further possibilities for the detection of probe/target interactions via insoluble precipitates in the method according to the invention are described in: Immunogold-Silver Staining, Principles, Methods and Applications, ed.: M. A. Hayat, 1995, CRC Press; *Eur J Immunogenet* 1991 February-April; 18(1-2): 33-55 HLA-DR, DQ and DP typing using PCR amplification and immobilized probes. Erlich H, Bugawan T, Begovich A B, Scharf S, Griffith R, Saiki R, Higuchi R, Walsh P S, Department of Human Genetics, Cetus Corp., Emeryville, Calif. 94608; *Mol Cell Probes* 1993 June; 7(3): 199-207 A combined modified reverse dot-blot and nested PCR assay for the specific non-radioactive detection of *Listeria monocytogenes*. Bsat N, Batt C A. Department of Food Science, Cornell University, Ithaca, N.Y. 14853. *Immunogenetics* 1990; 32(4): 231-41 Erratum in: *Immunogenetics* 1991; 34(6): 413 Rapid HLA-DPB typing using enzymatically amplified DNA and nonradioactive sequence-specific oligonucleotide probes. Bugawan T L, Begovich A B, Erlich H A. Department of Human Genetics, Cetus Corporation, Emeryville, Calif. 94608. *Hum Immunol* 1992 December; 35(4): 215-22 Generic HLA-DRB1 gene oligotyping by a nonradioactive reverse dot-blot methodology. Eliaou J F, Palmade F, Avinens O, Edouard E, Ballaguer P, Nicolas J C, Clot J. Laboratory of Immunology, Saint Eloi Hospital, CHU Montpellier, France. *J Immunol Methods* 1984 Nov. 30; 74(2): 353-60 Sensitive visualization of antigen-antibody reactions in dot and blot immune overlay assays with immunogold and immunogold/silver staining. Moeremans M, Daneels G, Van Dijck A, Langanger G, De Mey J. *Histochemistry* 1987; 86(6): 609-15 Non-radioactive in situ hybridization. A comparison of several immunocytochemical detection systems using reflection-contrast and electron microscopy. Cremers A F, Jansen in de Wal N, Wiegant J, Dirks R W, Weisbeek P, van der Ploeg M, Landegent J E.

Within the context of the present invention, the following variants among others are feasible for the detection of probe/target interactions using insoluble precipitates.

In one embodiment of the present invention, the targets are provided with a catalyst, preferably an enzyme, which catalyses the conversion of a soluble substrate into an insoluble product. The reaction which results in the formation of a precipitate on the array elements is in this case the conversion of a soluble substrate into an insoluble product in the presence of a catalyst, preferably an enzyme, coupled to the target. The enzyme is preferably selected from the group consisting of horseradish peroxidase, alkaline phosphatase and glucose oxidase. The soluble substrate is preferably selected from the group consisting of 3,3'-diaminobenzidine, 4-chlor-1-naphthol, 3-amino-9-ethylcarbazole, p-phenylene diamine-HCl/pyrocatechol, 3,3',5,5'-tetramethyl benzidine, naphthol/pyronine, bromochlorindoylphosphate, nitrotetrazolium blue and phenazine methosulphate. For example, a colourless soluble hydrogen donor, e.g. 3,3'-diaminobenzidine, is converted into an insoluble coloured product in the presence of hydrogen peroxide. The enzyme horseradish peroxidase transfers hydrogen ions from the donors to hydrogen peroxide with the formation of water.

In a preferred embodiment of the present invention the reaction which results in the formation of a precipitate on the array elements is the formation of a metal precipitate. Especially preferably the reaction resulting in the formation of a precipitate on the array elements is the chemical reduction of a silver compound, preferably silver nitrate, silver lactate, silver acetate or silver tartrate to elemental silver. Formaldehyde and/or hydroquinone are preferably used as reducing agents.

Especially preferably the precipitation of the metal compound takes place in the presence of metal clusters or colloidal metal particles coupled to the targets, especially gold clusters or colloidal gold particles, i.e. in this case the metal clusters or colloidal metal particles form the labelling coupled to the targets. For example, silver nitrate is converted into elemental silver, wherein silver ions accumulate from the solution on gold as a crystallisation nucleus and in a second step are reduced using a reducing agent such as formaldehyde or hydroquinone for example. An insoluble precipitate of elemental silver is thereby formed.

In an alternative embodiment, the precipitation of the metal compound takes place in the presence of poly-anions coupled to the targets. If the target itself is not a poly-anion, it is possible to use such a target for nucleus formation. The target labelled with a poly-anion is exposed for example to a silver nitrate solution. The silver cations then accumulate selectively on the poly-anion. Thereafter silver ions are converted into elemental silver using a reducing agent.

The coupling of the enzymes or catalysts or metal clusters or colloidal metal particles or poly-anions to the targets can be effected directly or via anchor molecules coupled to the targets. Basically, there is no need to provide the target directly with the aforementioned tags. It is also possible to achieve subsequent coupling of the tag via suitable anchor molecules, e.g. streptavidin which are coupled to the target.

A conjugate consisting of the respective catalyst or crystallisation nucleus and a specific binding partner for the anchor molecule can also be used to carry out the procedures described above. The reaction resulting in the formation of a precipitate on the array elements is then the binding of a specific binding partner to the anchor molecule coupled to the target.

Such binding partner/anchor molecule pairs are preferably selected from the group consisting of biotin/avidin or streptavidin or anti-biotin antibodies, digoxigenin/anti-digoxigenin immunoglobulin, FITC/anti-FITC immunoglobulin and DNP/anti-DNP immunoglobulin.

In each of the embodiments described hereinbefore, a soluble substrate is converted catalytically into an insoluble and precipitating product. As a result of the proximity to the surface, the product is precipitated directly on the surface and forms a solid precipitate insensitive to various washing procedures.

It is also possible within the context of the present invention that the labelling, especially the enzymes or metal clusters or colloidal metal particles or poly-anions, are coupled to the targets before, during or after the interaction with the probes.

In a preferred embodiment of the present invention, the interaction between the target and probe is a hybridisation between two nucleotide sequences. The hybridisation of the target with the probes arranged on a probe array also takes place according to a known standard protocol (see among others Lottspeich and Zorbas, 1998). The hybrids formed can be stabilised by covalent binding, for example, via psoralen intercalation and subsequent cross-linking or as described in U.S. Pat. No. 4,599,303 by non-covalent binding, for example, by binding of intercalators.

Hybridisation of the targets with the probes arranged on a probe array or the labelling of the hybridised targets is usually followed by a washing step with which unspecifically and therefore more weakly bound components are removed.

Alternatively, the interaction between the target and the probe is a reaction between an antigen structure and the corresponding antibody or a hypervariable region thereof or a reaction between a receptor and a corresponding ligand.

The binding or recognition of the targets by specific probes is usually a spontaneous non-covalent reaction under optimal conditions. Also included thereby are non-covalent chemical bonds. The composition of the medium as well as other chemical and physical factors influence the rate and strength of the binding. Thus, for example, in the case of nucleic acid recognition, a lower stringency and higher temperatures reduce the rate and strength of the binding between two non-perfectly complementary strands. It is also necessary to optimise the binding conditions for antigen/antibody or ligand/receptor interactions but the binding conditions are usually less specific.

In one embodiment of the present invention, the presence of a precipitate on an array element is detected by reflection, absorption or diffusion of a light beam, preferably a laser beam or a light-emitting diode, by the precipitate. As a result of its granular form, the precipitate modifies the reflection of a light beam. The precipitate also results in strong diffusion of light which can be recorded by conventional detection device. If the precipitate, for example, the silver precipitate, appears as a dark surface, the absorption of light can also be detected and recorded. The resolution of the detection then depends on the number of pixels of the camera. In an especially preferred embodiment the presence of a precipitate on an array element is detected, in which the light source homogeneously illuminates the array elements scanning at a scanning speed, wherein the scanning speed especially preferably ensures that an exposure time of the recording camera combines all the signals of the sample to form a single image.

For example, the regions intensified by the specific reaction can be detected by means of a very simple optical structure in transmitted light (contrast by shading) or in incident light (contrast by reflection). The detected intensity of the shaded region is directly proportional to the occupation density with the labelling such as gold particles for example and the nucleus formation state of the particles.

When using a precipitate which is electrically conductive or whose dielectric constant differs from the surroundings, in an alternative embodiment of the present invention, the reaction can also be detected electrically.

The electrical measurements can be made by means of conductivity measurements using micro-electrode array arrangements or using an arrangement of micro-capacitance sensors or by means of potential measurements using field effect transistor arrays (FET arrays). In conductivity measurements using micro-electrodes, the change in the electrical resistance between two electrodes is tracked during a precipitation reaction (E. Braun, Y. Eichen, U. Sivan, G. Ben-Yoseph, Nature, 775, vol 391, 1998). In the case of dielectricity measurements using micro-capacitance sensors the change in the capacitance of two electrodes arranged with respect to one another is measured (M. Madou, Fundamentals of Microfabrication, CRC Press, Boca Raton, 1997). In potential measurements using FET arrays the change in the potential on the sensor surfaces is measured (M. Madou, Fundamentals of Microfabrication, CRC Press, Boca Raton, 1997).

When using a substrate, which is radioactive or radioactively labelled, the presence of a precipitate on an array element can be detected by autoradiography, fluorography and/or indirect autoradiography. Thus, in autoradiography a surface covered with emitting precipitate is brought directly in contact with an x-ray film. In fluorography a surface covered with emitting precipitate is overlaid with fluorescent chemicals such as sodium salicylate which convert the radioactive radiation energy into fluorescence. In indirect autoradiography using intensifier screens, a surface covered by a β-emitting precipitate is placed on an intensifier screen which converts the radiation into blue light (see F. Lottspeich, H. Zorbas, see above). However, radioactivity-based detection methods are frequently undesirable because of the health risks and the safety regulations to be satisfied on this account.

In further alternative embodiments of the present invention, the presence of a precipitate on an array element is detected by scanning electron microscopy, electron probe micro-analysis (EPMA), magneto-optic Kerr microscopy, magnetic force microscopy (MFM), atomic force microscopy (AFM), measurement of the mirage effect, scanning tunneling microscopy (STM) and/or ultrasonic reflection tomography.

Detection of the reaction using SEM and/or EPMA is almost independent of the type of substrate. In scanning electron microscopy (SEM) a focussed electron beam scans the sample (J. Goldstein et al. Scanning Electron Microscopy and X-Ray Microanalysis, Plenum, New York, 1981). In electron probe microanalysis (EPMA) the secondary processes triggered by a focussed electron beam are used for spatially resolved analysis (J. Goldstein et al. Scanning Electron Microscopy and X-Ray Microanalysis, Plenum, New York, 1981).

When using a substrate, which is magnetic or tagged with magnetic particles, the reaction can be detected by magneto-optic Kerr microscopy or MFM. In magneto-optic Kerr microscopy the rotation of the polarisation plane of the light by magnetic fields is used (Kerr and Faraday effect) (A. Hubert, R. Schafer, Magnetic Domains, Springer, 1998).

The change in the optical density by the substrate on the surface as a result of the reaction can be detected by means of the mirage effect. In the mirage effect the local heating of a surface by absorption of a focussed laser beam is measured using the change in the refractive index associated therewith. An image of the local surface absorption properties is obtained by scanning the surface (A. Mandelis, Progress in Photothermal and Photoacoustic Science and Technology, Volume 1, Elsevier, New York 1992). Another thermal spatially resolved method for detecting the interaction reaction by the substrate is an array of microthermophiles, which measure the crystallisation or precipitation enthalpies of the substrate precipitates (J. M. Köhler, M. Zieren, Thermochimica Acta, 25, vol 310, 1998).

STM and AFM are also suitable for detecting the reaction by means of the substrate. In an atomic force microscope (AFM) a micro- or nanotip scans the surfaces, whereby the surface topography is measured (E. Braun, Y. Eichen, U. Sivan, G. Ben-Yoseph, Nature, 775, vol 391, 1998). The magnetic force microscope MFM detects local magnetic differences in susceptibility via a nanotip (A. Hubert, R. Schafer, Magnetic Domains, Springer, 1998). In a scanning tunneling microscope STM the tunnel current is measured using a nanotip to determine the nanosurface topography (O. Marti, M. Amrein, STM and SFM in biology, Academic Press Inc., San Diego, 1993).

More exotic methods such as ultrasonic reflection tomography can also be used. Tomographies are methods in which a three-dimensional image is compiled in a disk fashion (F. Natterer, Mathematical methods of computer tomography, Westdt. Vlg., Wiesbaden, 1997). In the case of ultrasonic reflection tomography the measurement of the ultrasonic reflection is used to produce the tomogram (V. Fleischer, F. Bergner, DGZFP NDT Conference Dresden 1997).

A further aspect of the present invention relates to a device for carrying out the method described previously, comprising:

a) at least one reaction vessel according to the invention described previously; and
b) a detection device for detecting the specific interaction.

When using a staining method having a reactively intensifying effect for the interaction, such as the immunogold/silver staining described previously, unlike the fluorescence measurements usually used, detection can be carried out by simple absorption or reflection measurements so that the total costs of the device according to the invention are very low.

The device according to the invention is preferably used in a detection method in which, as described previously, detection takes place via a reaction which results in a precipitate on the array elements on which an interaction between probes and targets has taken place. In the reaction vessel which can be inserted in the detection device or the reader, interaction products in the form of a precipitate are formed on some array elements as a result of the specific interaction of the sample or the target with the probes. These interaction products have a different absorption coefficient compared with the pure substances. This effect can be intensified considerably by means of suitable reactions, as described previously.

The detection device is preferably a camera, especially a CCD or CMOS camera or similar camera which usually records the entire region of the probe array. Alternatively, scanning methods can also be used for the detection device for reading out the reaction vessel.

In special embodiments of the device according to the invention the detection device additionally comprises readout optics.

In a preferred embodiment, the device according to the invention also comprises at least one light source. A light source within the context of the present invention preferably ensures homogeneous illumination of the support. The light source is especially preferably selected from the group consisting of lasers, light-emitting diodes (LED), surface emitters and high-pressure lamps.

In addition to point source of light, light sources in the form of illuminating arrays can also be used in the device according to the invention. In this embodiment homogeneous illumination of the support can be ensured for example by the fact that the light source comprises a plurality of diffusely emitting light sources whose superposition results in homogeneous illumination. Thus, for example, diffusely scattering LED which are arranged in a matrix form make it possible to achieve homogeneous illumination at short distances from the sample.

Homogeneous illumination can also be achieved by suitable structuring of the lid of the reaction vessel according to the invention. In this way, the lid of the reaction vessel according to the invention takes on the function of a diffusing disk/lens.

In a further preferred embodiment of the invention the light source is mounted in a swivel arm which can be swivelled aside for insertion of the reaction vessel into the device. It can thereafter be swivelled over the reaction vessel to illuminate the affinity matrix. In this way the reaction vessel can be pressed into a reaction vessel holder so that the substance library lies in the correct image plane. Re-focussing the imaging optics or readout optics thereby becomes superfluous. Alternatively, the reader or the detection device can be equipped with a focussing device so that different types of reaction vessels can be recorded.

In another embodiment an adjusting recess into which the lid of the reaction vessel can be pressed is located in the device according to the invention. Twisting of the affinity matrix is thereby avoided.

The components of an exemplary structure of a device according to the invention for optical detection of a precipitate formation consist of a low-power (500 mcd) light source, e.g. an LED, for homogeneous illumination and a detector, e.g. a CCD camera. As a result of the intensification effect via the catalytic precipitation of the substrate, especially when using a gold/silver system, the changes in the optical properties of the surface are marked such that a simple flat bed scanner, a slide scanner or a comparable device is sufficient to detect the precipitate.

Typical detection times are significantly less than one second whereas comparable sensitive CCD systems for detecting fluorescence require about 10-18 seconds so that cheap consumer cameras can be used whose signal transmission corresponds to the video standard.

In a further advantageous embodiment of the device according to the invention, the device additionally comprises optical filters. Such filters on the one hand make it possible to spectrally limit the homogeneous illumination and on the other hand to illuminate the samples with different wavelengths. In a further variant the device according to the invention additionally comprises filter changers. With these filter changers the optical filters can be changed quickly and thus possible incorrect information which occurs as a result of impurities for example is uniquely recognised and eliminated.

In a further preferred embodiment, especially if the reflectivity of the supporting element is measured, the device additionally comprises a semitransparent mirror between light source and supporting element. In this embodiment the light from the light source passes through a semitransparent mirror onto the sample and the image is imaged in reflection by the semi-transparent mirror and if necessary, the readout optics onto a camera.

In a preferred embodiment for measuring the reflectivity, a surface mirror is additionally located on the underside of the supporting element. In this embodiment the disadvantage of the poor reflection of the sample is supplemented by transmission effects wherein the illuminating light is reflected via a mirror layer behind the sample either as an independent mirror or as a layer deposited on the backside of the sample support. In this case, for example, a surface emitter can be arranged on the opposite side of the supporting element and thus also to the sensor of a CCD camera, for example. In this way, a very compact arrangement is made possible.

In a further embodiment the sample is located in a cell which has direct contact with the sensor of a CCD camera by means of readout optics. In this case, the readout optics or the coupling medium between cell and camera is preferably a fibreboard available for example from Schott or an image cable or image line. In this embodiment the reaction vessel according to the invention is a cell consisting of two plane-parallel plates with intermediary sample volumes. The chip with the surface-bound substance library is inserted in this cell and can be read out like cells in a spectrometer.

Preferably the device according to the invention additionally has a temperature-control unit which ensures that the sample is stored at a stable temperature during the measurement. This ensures that the results are reproducible.

In another embodiment a plurality of reaction vessels are arranged in the device such that successive detection is ensured. For example, temporally staggered, successive readout can be achieved by arranging the samples in the form of magazines or a carousel in the device according to the invention.

It is furthermore preferred that the device according to the invention additionally comprises a computer which is programmed to:
collect the signal intensities recorded by the detection device; and
if necessary to convert the signal intensities into an analogue image.

Within the context of the present invention an image is understood as a group of pixels which represents an illustration of the measured signal intensities for a probe array and which can be transmitted directly, for example, to a screen or a printer for recording.

As has already been described in detail previously, the dynamic resolution of the measurement data can be increased extremely even, when using an 8-bit detection technique, by time-resolved detection during the intensification process by the deposition of a precipitate, such as elemental silver for example, on gold particles acting as crystallisation nuclei, and calculating the relative occupation densities from the time behaviour using the method according to the invention. The structure of the device required for this differs by the mechanical recording of a reaction chamber and modified acquisition software. The software, for example Iconoclust® software (Clondiag), is characterised in that successively obtained recordings are processed. For this purpose, the grey values determined using the individual probe array elements are determined at each measurement time. For all array elements the virtual signal intensity is calculated time-dependently as a function of the precipitate formation. Starting from this value, for example, the grey values of the last measurement are brought into relationship with the product of the rate and measurement time. A spread of the measurement range is thereby achieved. Thus, even when using a cheap 8-bit camera, excellent resolution of weak as well as strong probe/target interactions as well as precise quantification of the bound target is achieved.

The potential for miniaturisation of such a structure is very high so that said entire system can be designed as an independent hand-held device for use in the field. Furthermore, in an especially preferred embodiment the device according to the invention can also be realised as a highly integrated independent unit. Thus, highly sensitive applications of microarrays such as, for example, medical diagnostics, forensics, bacterial screening and the like can be carried out quickly by laymen independently of medical and biological laboratories.

The reaction vessel according to the invention thus comprises a standard laboratory reaction vessel or standard micro-tube with a support or chip or array inserted on one of the base surfaces, e.g. on the bottom or in the lid of a conventional reaction vessel, such as a commercially available Eppendorf tube for example. This arrangement allows substantially easier handling and higher reproducibility. Solutions can easily be pipetted into the reaction vessel according to the invention and can be incubated and processed, e.g. centrifuged using microtube equipment available in almost every laboratory, especially in molecular biology laboratories.

Special embodiments of the device according to the invention are explained in detail below with reference to the drawings:

FIGS. 5 to 12 illustrate various optical principles which can be used to read out surface-bound substance libraries (102). In the reaction vessel used in the detection and reading equipment, a specific interaction of the sample or target with probes of some library elements of the substance library (102) takes place, whereby interaction products are formed on some surfaces.

These interaction products have different absorption coefficients to pure substances wherein this effect can be intensified considerably by suitable reactions. The absorption or reflection ratios of the surface-bound substance libraries before, during and/or after the interaction reaction are imaged by the readout systems (1000) shown in FIGS. 5 to 17.

In FIGS. 5 to 12 the representation of the reaction vessel (1) is restricted to the representation of the surface-bound substance libraries (100) for a better illustration of the readout principle. FIGS. 13 to 17 show two specific embodiments for imaging a precipitate on surface-bound substance libraries (100). Instead of the readers (1000) shown here, scanning methods can also be used to read out the reaction vessel (1).

Furthermore, the description of FIGS. 5 to 17 is given with reference to the use of DNA chips (100) in conjunction with the silver precipitation reaction described previously, but of course is not restricted to this.

FIG. 5 shows the fundamental arrangement of a device according to the invention for reading out the reaction vessel (1). Light from an incoherent light source (1001) illuminates the surface-bound DNA library on a library chip (100) located inside a tube (1) by means of illuminating optics (1002). The signal is recorded by a CCD camera (1005) using readout optics (1004).

FIG. 6 shows the same arrangement as in FIG. 5 with the variant of restricting the spectral range of the illumination by inserting optical filters (1006) in the optical path of the illuminating beam. Light from an incoherent light source (1001) illuminates the surface-bound DNA library on a library chip (100) located in a reaction vessel (1) using illuminating optics (1002). The signal is recorded by a CCD camera (1005) using readout optics (1004). The opportunity of changing these filters quickly using a filter changer (1007) has the advantage for the evaluation that any incorrect information, which for example may be caused by contaminations, can be clearly identified and eliminated.

In the device shown in FIG. 7 the point light source (1001) is replaced by an illuminating array (1008). Light from an illuminating array (1008) homogeneously illuminates the surface-bound DNA library (102) on a library chip (100) located in a reaction vessel (1) using illuminating optics (1002). The signal is recorded by a CCD camera (1005) using readout optics (1004). Preferably, diffusely scattering LED, arranged in matrix form, make it possible to achieve homogeneous illumination at short distances relative to the sample.

In the arrangement of the device according to the invention as shown in FIG. 8, a compact reader (1000) is shown in which the CCD sensor (1005) of the camera is directly in contact with the affinity matrix (100). This contact can also be produced by using a fibreboard (1012) or at still greater distances by using an image cable if direct contact is not possible. Light from an incoherent light source (1001) illuminates the surface-bound DNA library on a library chip (100) located in a reaction vessel (1) using illuminating optics (1002). The signal from the sample is recorded directly by a CCD camera (1005).

In the reader (1000) shown in FIG. 9 the samples are measured in incident light. Unlike the readers or detection devices (1000) described previously, the reflectivity of the DNA library (102) is measured with this device. Light from an incoherent light source (1001) illuminates the surface-bound DNA library on a library chip (100), which is located in a reaction vessel (1), using illuminating optics (1002) through a semitransparent mirror. The reflected signal is deflected onto the readout optics (1004) by the semitransparent mirror (1009) and from there is imaged onto a CCD camera (1005).

Since the silver precipitate does not possess very good reflection properties, the arrangement shown in FIG. 10 is advantageous in incident-light measurements. Light from an incoherent light source (1001) illuminates the surface-bound DNA library (102) on a library chip (100) located in a reaction vessel (1) using illuminating optics (1002) through a semitransparent mirror. The reflected signal is deflected onto the readout optics (1004) by the semitransparent mirror (1009) and from there is imaged onto a CCD camera (1005). The disadvantage of the poor reflection of the sample is supplemented by transmission effects whereby the illuminating light is reflected via a mirror layer (1010) behind the sample, either as an independent mirror or as a layer applied on the backside of the sample carrier.

FIG. 11 shows the possible arrangement of the device according to the invention in a transparent sample space, preferably in a cell (1011) which makes it possible to achieve good coupling of the receiver to the sample space by means of the fibreboard (1012) through the optically plane outer surfaces. Light from an incoherent light source (1001) illuminates the surface-bound DNA library (102) on a library chip (100) through the transparent wall of the cell using illuminating optics (1002). Through the transparent wall of the cell the signal from the sample is recorded directly by a CCD camera (1005). A fibreboard (1012) or an image line can be used as coupling medium between cell and CCD camera.

The device shown in FIG. 12 represents a very compact arrangement of the reader (1000) shown in FIG. 11. Very compact sensors can be realised when using diffuse surface emitters (1013), which for example are based on electroluminescence or cold cathode fluorescence methods. In this case of a diffuse light emitter (1013), light from an incoherent light source (1001) directly illuminates the library chip (100) through the transparent wall of the cell. The signal from the sample is recorded directly by a CCD camera (1005).

FIGS. 13 and 14 show an exemplary embodiment in which a reader (1000) is shown in plan view and in sectional view. The working principle corresponds to that of the device shown in FIG. 1. A deflecting mirror was installed between the affinity matrix (100) and the imaging optics (1004) to achieve compact equipment dimensions. The light from the light source (1008) shines into the reaction vessel (1) and then through the DNA chip (100) onto a deflecting mirror. From there the image of the DNA chip (100) is projected via the imaging optics (1004) onto a CCD camera (1005). The light source (1008) consists of light-emitting diodes built into a swivel arm which can be swivelled aside to insert the reaction vessel (1) into the reader (1000). Thereafter it is swivelled over the reaction vessel (1) to illuminate the affinity matrix (100). In this case, it presses the reaction vessel (1) into the reaction vessel holder (1100) so that the DNA library (102) lies in the correct imaging plane. Re-focussing of the imaging optics (1004) is thereby superfluous. Located on the upper side is an adjusting recess (1102) into which the lid of the reaction vessel (1) is pressed. Twisting of the affinity matrix (102) is thereby avoided. A Peltier element (1200) is located at the reaction vessel holder (1100) in order to keep the conditions in the reaction vessel (1) reproducible. The temperature in the reaction vessel (1) can thereby be regulated. The reaction vessel holder (1100) can additionally be provided with resistance heating in order to be able to set higher temperatures. Alternatively, the reaction vessel holder (1100) can also be tempered with circulating cooling media.

FIG. 15 shows a reader (1000) which differs from that in FIG. 13 by the fact that the swivel arm (1101) is replaced by a slider (1300). The slider (1300) is slid over the reaction vessel (1) via a linear bearing (1310). In this case, a moving carriage (1320) pushes the reaction vessel (1) into the reaction vessel holder (1100) by means of four compression springs (1321). An adjusting gap (1322) embraces the lid (3) of the reaction vessel (1) such that the reaction vessel (1) is turned into its correct position and fixed by the sliding movement of the slider (1300). In FIG. 17 the position of the slider (1300) to the reaction vessel (1) is shown with the reader open. The moving carriage (1300) moves along the arrow shown there and thereby closes the reaction vessel (1). At the same time the light source (1008) is slid over the reaction vessel (1) so that measurements can be made using the reader (1000). When the slider (1300) is closed, the carriage (1320) is positioned between the light source and reaction vessel (1). The moving carriage thus has a detection opening (1323) in order to be able to illuminate the affinity matrix (100).

The following examples are used to illustrate the invention and are by no means to be understood as restrictive.

EXAMPLES

Example 1

Manufacture of the Reaction Vessel (1)

A standard reaction test tube from Eppendorf made of polypropylene and having a nominal receiving volume of 1.5 ml was used for re-melting. For this purpose the reaction tube was capped on the bottom side and some material was turned off from the sides. The tube was then placed on a pin and pressed under force onto a hot mould which impressed the opening or the recess (8), the chip support (6) as well as the adhesive edge (7) into the tube (see FIG. 1).

Example 2

Detection and Specificity of the Hybridisation of Nucleic Acids in the Reaction Vessel (1) Using Silver Detection a) Test System The human cyp2D6 gene codes for a human cytochrome P450. This enzyme plays an important role in the metabolism of various drugs and active agents. Mutations in the cyp2D6 gene may result in hypersensitivity or intolerance for certain medicaments. At least 14 of such mutations (point mutations and deletions) are described for cyp2D6. For a selection of these mutations (G1749C, dT1795, G1934A, G2064A) it is to be tested whether the respective wild type or the mutations are present in a sample to be analysed.

b) Production of the DNA Library (102) and Assembly with the Reaction Vessel (1)

Using a MicroGrid II Arrayer (BioRobotics, Cambridge, Great Britain), 40 amino-modified oligonucleotides (probes) having a length of 21-25 nucleotides were deposited at defined sites on an epoxidized glass surface (slide size: 75 mm×25 mm) (101) and covalently immobilised (library or array elements). The probes were divided into pairs of library elements, wherein the first respectively represents the wild type and the second the mutation.

The oligonucleotide sequences were as follows (sequence in 5'-3' direction with 5'-NH$_2$ modification):

| Name | Sequence |
|---|---|
| G1749C-WT | GCTTCTCCGTGTCCACCTTGC |
| G1749C | GCTTCTCCGTCTCCACCTTGC |
| G1749C-WT-2 | GCGCTTCTCCGTGTCCACCTT |
| G1749C-2 | GCGCTTCTCCGTCTCCACCTT |
| G1749C-WT-4 | AGGCGCTTCTCCGTGTCCACC |
| G1749C-4 | AGGCGCTTCTCCGTCTCCACC |
| G1749C-WT+2 | TTCTCCGTGTCCACCTTGCGC |
| G1749C+2 | TTCTCCGTCTCCACCTTGCGC |
| G1749C-WT+4 | CTCCGTGTCCACCTTGCGCAA |
| G1749C+4 | CTCCGTCTCCACCTTGCGCAA |
| dT1795-WT | GCTGGAGCAGTGGGTGACCGA |
| dT1795 | GCTGGAGCAGGGTGACCGAG |
| dT1795-WT-2 | TCGCTGGAGCAGTGGGTGACC |
| dT1795-2 | TCGCTGGAGCAGGGGTGACCG |
| dT1795-WT-4 | AGTCGCTGGAGCAGTGGGTGA |
| dT1795-4 | AGTCGCTGGAGCAGGGGTGAC |
| dT1795-WT+2 | TGGAGCAGTGGGTGACCGAGG |
| dT1795+2 | TGGAGCAGGGGTGACCGAGGA |
| dT1795-WT+4 | GAGCAGTGGGTGACCGAGGAG |
| dT1795+4 | GAGCAGGGGTGACCGAGGAGG |
| G1934A-WT | CCCACCCCCAGGACGCCCCTT |
| G1934A | CCCACCCCCAAGACGCCCCTT |
| G1934A-WT-2 | CTCCCACCCCCAGGACGCCCC |
| G1934A-2 | CTCCCACCCCCAAGACGCCCC |
| G1934A-WT-4 | ATCTCCCACCCCCAGGACGCC |
| G1934A-4 | ATCTCCCACCCCCAAGACGCC |
| G1934A-WT+2 | CACCCCCAGGACGCCCCTTTC |
| G1934A+2 | CACCCCCAAGACGCCCCTTTC |

-continued

| Name | Sequence |
|---|---|
| G1934A-WT+4 | CCCCCAGGACGCCCCTTTCGC |
| G1934A+4 | CCCCCAAGACGCCCCTTTCGC |
| G2064A-WT | TAGCTCAGGAGGGACTGAAGGAGGA |
| G2064A | TAGCTCAGGAGGAACTGAAGGAGGA |
| G2064A-WT-2 | CCTAGCTCAGGAGGGACTGAAGGAG |
| G2064A-2 | CCTAGCTCAGGAGGAACTGAAGGAG |
| G2064A-WT-4 | GACCTAGCTCAGGAGGGACTGAAGG |
| G2064A-4 | GACCTAGCTCAGGAGGAACTGAAGG |
| G2064A-WT+2 | GCTCAGGAGGGACTGAAGGAGGAGT |
| G2064A+2 | GCTCAGGAGGAACTGAAGGAGGAGT |
| G2064A-WT+4 | TCAGGAGGGACTGAAGGAGGAGTCG |
| G2064A+4 | TCAGGAGGGACTGAAGGAGGAGTCG |

A single complete (rectangular) DNA library (102) on the slide surface (101) consisted of a total of 12×10=120 deposited library elements and 7 tags for optical orientation of the image of the reader (1000). Each of the 40 oligonucleotide probes was deposited in threefold repetition on the DNA library (102) (for the arrangement of the library elements see FIG. 18). The library elements had a spacing of 0.2 mm, the total DNA library (102) covered an area of 2.4 mm×2.4 mm. In total, more than 100 identical DNA libraries (102) could be produced in this way per slide.

The library elements were deposited on the slides from a respectively 10 µM solution of the oligonucleotides in 0.1 M phosphate buffer/2.2% sodium sulphate. The library elements were then linked covalently to the epoxide groups on the glass surface by baking for 30 minutes at 60° C. This was followed by a multi-step washing process in the following order:

5 min in 600 ml double-distilled $H_2O$+600 µl Triton ×100
  2×2 min in 600 ml double-distilled $H_2O$+60 µl HCl (conc.)
  30 min in 100 mM KCl solution
  rinsing in double-distilled $H_2O$ for 1 min
  drying with compressed air After completion of the washing and drying steps of the slides, they were cut into 3.15 mm×3.15 mm glass pieces (hereinafter called DNA chips (100)). Exactly one DNA library (102) having the dimensions of 2.4 mm×2.4 mm was located on each of the chips (100). The chips (100) were then inserted into the reaction vessel (1) in the manner shown in FIG. 1 and glued with polydimethyl siloxane which was given into the adhesive edge (7).

c) Preparation of the Targets for Hybridisation Against the DNA Libraries

The sample to be analysed (hereinafter called target) was a biotin-labelled PCR of a patient DNA directed towards the exon 3/4 of cyp2D6 (KDL24, genotyped by sequencing as wild type for the mutations concerned). The PCR mixture was as follows:
  Primer 1: cyp2D6_3/4-f, sequence 5'-CACGCGCACGT-GCCCGTCCCA-3' (SEQ ID NO: 41), final concentration 200 nM
  Primer 2: cyp2D6_3/4r-5'Bio, sequence 5'-Bio-CTCTCGCTCCGCACCTCGCGCAGA-3' (SEQ ID NO: 42), final concentration 200 nM
  dNTPs, final concentration 200 µM
  Advantage cDNA-Polymerase-Mix (50-fold, Clontech, Palo Alto, USA), final concentration 1-fold
  Advantage cDNA PCR reaction buffer (10-fold, Clontech, Palo Alto, USA), final concentration 1-fold
  Template DNA (KDL24), 80 ng
  Water to 50 µl The PCR was then carried out using the following program:
  1 Denaturing (10 min, 95° C.)
  2 Denaturing (30 s, 95° C.)
  3 Annealing (30 s, 65° C.)
  4 Elongation (80 s, 72° C.)
  5 29 times repetition of steps 2-4
  6 Elongation (7 min, 72° C.)
  7 Cooling (4° C., until further treatment)

d) Hybridisation and Conjugation of the Probe Array in the Reaction Vessel (1)

For the hybridisation reaction in the reaction vessel (1) 4 µl of the PCR product obtained were mixed with 146 µl 6×SSPE buffer (52.59 g NaCl, 8.28 g $NaH_2PO_4$×$H_2O$, 2.22 g EDTA× $2H_2O$ in 1 L double-distilled $H_2O$, adjusted to pH 7.4 with NaOH)/0.1% SDS and added to the ready-assembled reaction vessel (1). After denaturing the hybridisation solution (5 min, 95° C.), incubation was carried out for 60 min at 65° C. with gentle shaking. The hybridisation solution was then removed from the reaction vessel (1). This was followed by two washing steps: 10 min each in 2×SSC/0.2% SDS (500 µl at 30° C.) and 2×SSC (500 µl at 20° C.). The prepared conjugation solution (Streptavidin-Gold, British Biocell International, EM.STP5, final concentration 250 pg/µl in 6×SSPE/0.1% SDS) was then added to the chip (100) in the reaction vessel (1) and the reaction vessel (1) was incubated for 15 min at 37° C. After removal of the conjugate solution, the chip (100) in the reaction vessel (1) was washed for 10 min each in 2×SSC/ 0.2% SDS (500 µl at 30° C.), 2×SSC (500 µl at 20° C.) and 0.2×SSC (500 µl at 20° C.) whilst shaking.

e) Detection

For the silver intensification the built-in chip (100) in the reaction vessel (1) was covered with a silver developing solution (British Biocell International, SEKL15, Cardiff, Great Britain) and the reaction vessel (1) was inserted in the silver reader (1000). The reader (1000) consists of a sample receiver with tempering, the readout section and a swivel arm (1101) with the illumination (see FIGS. 13 and 14). The samples were illuminated in transmitted light using a diffusely illuminating array of a plurality of LED (1008). An additional diffuser allowed uniform illumination of the samples with deviations of less than 10% from the maximum.

The sample was read out in transmission. For this purpose the samples were inserted in the receiver provided. Correct positioning of the samples was ensured by specially shaping the receiver (1102). The reaction vessel (1) was inserted therein with the closure opened. In this position the lid of the reaction vessel (1) does not allow any twisting of the affinity matrix (100). The illumination can only be swivelled into the measuring position when the position is correct. In the measuring position the swivel arm simultaneously fixes the reaction vessel (1) and thus the affinity matrix.

For the evaluation method it has proved advantageous to use distortion-free readout optics (1004) for reading out. By using optics with a large field depth, there was no need for any adjustment of the samples relative to the camera. Focussing was superfluous. Depending on the density of the substances per unit area on the affinity matrix, the CCD camera (1005) used is either in CCIR format or in even higher resolution. During the measurement the samples were kept temperature-stable by resistance heating and a Peltier element (1200).

The silver developing solution was produced by mixing equal parts of initiator and enhancer solutions. During the 20 minute incubation time at 25° C. (±0.1° C.) the time response of the silver intensification was documented by a series of photographs (an image every 10 s) (see FIG. 19).

The optical density of the library elements of all images in the time series was determined using the image evaluation software IconoClust® from Clondia®. FIG. 20 shows the time series for the element G1934A+4 (mutation) and G2064A-WT (wild type).

The measured values $\alpha_{G1934A+4}$ and $\alpha_{G2064A-WT}$ were calculated in accordance with the procedure for the evaluation given in the description. These were $\alpha_{G1934A+4}=4.83*10^{-7}$ sec$^{-2}$ and $\alpha_{G2064A-WT}=2.566*10^{-6}$ sec$^{-2}$.

REFERENCE NUMBERS

1 Reaction vessel
2 Reaction vessel with an opening (recess) shaped as an enclosure to receive affinity matrices
3 Lid
4 Connecting strip
5 Seal
6 Chip support outside
7 Adhesive edge outside
8 Liquid opening
9 Adhesive edge inside
10 Viewing opening
11 Chip support inside
100 Library chip, affinity matrix or DNA chip
101 Substrate
102 Surface-bound substance library
200 Chip support
201 Clamping connection
300 Clamping sleeve
301 Sealing surfaces
1000 Reader
1001 Light source
1002 Illuminating optics
1004 Readout optics
1005 Sensor, preferably a CCD camera
1006 Optical transmission filter
1007 Filter changer
1008 Illuminating array, preferably an arrangement of LED
1009 Semitransparent mirror
1010 Mirror or mirror-coating of the support of the DNA library
1011 Cell
1012 Fibreboard
1013 Diffuse surface emitter
1014 Deflecting mirror
1100 Reaction vessel holder
1101 Swivel arm
1102 Adjusting recess
1200 Peltier element
1300 Slider
1310 Linear bearing
1320 Moving carriage
1321 Compression spring
1322 Adjusting gap
1323 Detection opening
1324 Bearing surface

The invention claimed is:

1. A reaction vessel for detecting interactions between a molecular target and probe molecules, comprising a tube having
a generally cylindrical free-standing wall comprising an opening configured to receive a sample and a base portion spaced apart from the opening by the cylindrical wall,
a lid attached to the cylindrical wall via a connecting strip and configured to seal the opening and fit into an adjusting recess of a reader,
a void located in the base portion opposed to the opening,
a substrate secured within the void with a clamping connection or clamping sleeve to the base portion, the substrate comprising an inner surface enclosed except for the opening by the cylindrical wall and an outer surface disposed externally of the cylindrical wall, and
probe molecules immobilised on predetermined regions of the inner surface, the probe molecules being configured to interact with the molecular target;
wherein the connecting strip has a length,
wherein the reaction vessel has a height of at least 1.5 cm.

2. The reaction vessel of claim 1, wherein the base further comprises a recess for receiving the supporting element.

3. The reaction vessel of claim 1, wherein the inner surface is optically transparent.

4. The reaction vessel of claim 3 wherein the outer surface is optically transparent.

5. The reaction vessel of claim 1, wherein the substrate comprises glass and/or silicon.

6. The reaction vessel of claim 1, wherein the substrate comprises a material selected from the group consisting of Borofloat 33, quartz glass, mono-crystalline $CaF_2$ and mono-crystalline silicon.

7. The reaction vessel of claim 1, wherein the substrate comprises a material selected from the group consisting of glass, glass-ceramics, plastic-coated glass, plastics, rubber, and metals.

8. The reaction vessel of claim 7, wherein the plastic is selected from the group consisting of polypropylene, polyethylene, polystyrene, polycarbonate, PVC, polymethylmethacrylate, polytetrafluoroethylene, nylon and silicone plastic.

9. The reaction vessel of claim 7, wherein the metal is selected from the group consisting of stainless steels, platinum and aluminum, and mixtures thereof.

10. The reaction vessel of claim 1, comprising a filling volume in the range of from 100 µl to 2.5 ml.

11. The reaction vessel of claim 10, wherein the filling volume is 1.5 ml.

12. The reaction vessel of claim 1, wherein the immobilised probe molecules comprise a substance library selected from the group consisting of protein libraries, peptide libraries and nucleic acid libraries.

13. The reaction vessel of claim 12, wherein the substance library is a protein library selected from the group consisting of an antibody library, a receptor protein library and a membrane protein library.

14. The reaction vessel of claim 12, wherein the substance library is a peptide library selected from the group consisting of a library of receptor ligands, a library of pharmacologically active peptides and a library of peptide hormones.

15. The reaction vessel of claim 12, wherein the substance library is a nucleic acid library selected from the group consisting of a DNA molecule library and an RNA molecule library.

16. The reaction vessel of claim 1, wherein the probe molecules comprise oligonucleotides having a length of 15 to 50 bases.

17. The reaction vessel of claim 1, wherein the probe molecules comprise oligonucleotides having a length of 20 to 30 bases.

18. A device for detecting a specific interaction between a molecular target and probe molecules, comprising:
　a) the reaction vessel of claim 1; and
　b) a detection device for detecting the specific interaction.

19. The device of claim 18, wherein the detection device comprises a camera.

20. The device of claim 19, wherein the detection device further comprises readout optics.

21. The device of claim 19, wherein the camera is a CCD or CMOS camera.

22. The device of claim 18, further comprising a light source.

23. The device of claim 22, wherein the light source homogeneously illuminates the substrate.

24. The device of claim 22, wherein the light source is an illuminating array comprising a plurality of diffusely emitting light sources which ensure homogeneous illumination of the substrate by spectral interference.

25. The device of claim 22, wherein the light source is selected from the group consisting of lasers, light-emitting diodes (LED), surface emitters and high-pressure lamps.

26. The device of claim 18, wherein the reaction vessel further comprises a structured lid to ensure a homogeneous illumination of the substrate.

27. The device of claim 18, further comprising optical filters.

28. The device of claim 27, further comprising optical filter changers.

29. The device of claim 22, further comprising a semitransparent mirror positioned between the light source and the substrate.

30. The device of claim 18, wherein the reaction vessel is in direct contact with the detection device.

31. The device of claim 18, comprising a plurality of the reaction vessels arranged such that successive detection is ensured.

32. The device of claim 18, further comprising a temperature control unit.

33. The device of claim 18, further comprising a computer that is programmed for collecting signal intensities recorded by the detection device.

34. The device of claim 33, wherein the computer is additionally programmed for ensuring conversion of virtual signal intensities into an analogue image.

35. A method for detecting the specific interaction between a molecular target and probe molecules, comprising:
　a) providing the device of claim 18;
　b) interacting the molecular target with the probes; and
　c) detecting the interaction.

36. The method of claim 35, wherein the detecting comprises carrying out a reaction that results in a precipitate on the array elements on which the interaction occurs.

37. The method of claim 36, wherein a time profile of formation of the precipitate is detected on the array elements in a form of signal intensities.

38. The method of claim 36, wherein the reaction comprises conversion of a soluble substrate into a metallic precipitate.

39. The method of claim 38, wherein the reaction comprises chemical reduction of a silver compound to form elemental silver.

40. The method of claim 39, wherein the silver compound is selected from the group consisting of silver nitrate, silver lactate, silver acetate and silver tartarate.

41. The method of claim 39, wherein the reaction is carried out in the presence of a reducing agent selected from the group consisting of formaldehyde and hydroquinone.

42. The method of claim 38, wherein the reaction takes place in the presence of metal clusters or colloidal metal particles coupled to the molecular target.

43. The method of claim 42, wherein the metal comprises gold.

44. The method of claim 42, wherein coupling of the metal clusters or colloidal metal particles to the molecular target takes place directly or via anchor molecules coupled to the molecular target.

45. The method of claim 35, wherein the molecular target and the probes each comprise a nucleotide sequence and the interaction comprises hybridisation between the molecular target and the probes.

46. The method of claim 36, wherein the detecting of the presence of a precipitate on the array elements is effected by reflection, absorption or diffusion of a light beam by the precipitate.

47. The method of claim 46, wherein the light beam comprises a laser beam or a light-emitting diode.

48. The method of claim 35, wherein the molecular target is disposed on a microarray.

49. A reaction vessel for detecting interactions between a molecular target and probe molecules, comprising a tube having
　a generally cylindrical free-standing wall comprising an opening configured to receive a sample and a base portion spaced apart from the opening by the cylindrical wall,
　a lid attached to the cylindrical wall via a connecting strip configured to seal the opening and fit into an adjusting recess of a reader, the lid comprising an inner surface enclosed by the tube when sealed, and
　probe molecules immobilised on predetermined regions of the inner surface having a clamping connection or clamping sleeve, the probe molecules being configured to interact with the molecular target;
　wherein the connecting strip has a length,
　wherein the reaction vessel has a height of at least 1.5 cm.

50. The reaction vessel of claim 49, wherein the probe molecules comprise oligonucleotides having a length of 15 to 50 bases.

51. The reaction vessel of claim 49, wherein the probe molecules comprise oligonucleotides having a length of 20 to 30 bases.

52. A reaction vessel comprising:
　a generally cylindrical free-standing wall comprising an opening configured to receive a sample and a base portion spaced apart from the opening by a cylindrical wall,
　a lid attached to the cylindrical wall via a connecting strip and configured to seal the opening and fit into an adjusting recess of a reader, the reaction vessel defining a volume when sealed of at least 100 μL and 2.5 mL or less, a void located in the base portion opposed to the opening, an impermeable transparent substrate secured within the void with a clamping connection or clamping sleeve to the base portion, the substrate comprising an inner surface enclosed except for the opening by the cylindrical wall and an outer surface disposed externally of the cylindrical wall, and probe molecules immobilized at each of multiple spaced-apart predetermined regions of the inner surface, the probe molecules of different locations being configured to interact with a different molecular target;

wherein the connecting strip has a length, wherein the reaction vessel has a height of at least 1.5 cm.

53. The reaction vessel of claim 52, wherein the probe molecules comprise oligonucleotides having a length of 15 to 50 bases.

54. The reaction vessel of claim 52, wherein the probe molecules comprise oligonucleotides having a length of 20 to 30 bases.

\* \* \* \* \*